United States Patent
Kwon

(10) Patent No.: US 9,631,012 B2
(45) Date of Patent: Apr. 25, 2017

(54) ANTIBODIES AGAINST TM4SF5 AND METHODS OF USE THEREOF

(71) Applicant: Industry Academic Cooperation Foundation, Hallym University, Chuncheon (KR)

(72) Inventor: Hyung-Joo Kwon, Cheongju-si (KR)

(73) Assignee: Industry Academic Cooperation Foundation, Hallym University, Chuncheon (KR)

( * ) Notice: Subject to any disclaimer, the term of this patent is extended or adjusted under 35 U.S.C. 154(b) by 0 days.

(21) Appl. No.: 14/770,317

(22) PCT Filed: Feb. 26, 2014

(86) PCT No.: PCT/KR2014/001567
§ 371 (c)(1),
(2) Date: Aug. 25, 2015

(87) PCT Pub. No.: WO2014/133316
PCT Pub. Date: Sep. 4, 2014

(65) Prior Publication Data
US 2016/0002322 A1 Jan. 7, 2016

(30) Foreign Application Priority Data

Feb. 26, 2013 (KR) .................. 10-2013-0020547

(51) Int. Cl.
| C07K 16/18 | (2006.01) |
| C07K 16/30 | (2006.01) |
| C07K 16/28 | (2006.01) |
| G01N 33/68 | (2006.01) |
| A61K 39/00 | (2006.01) |

(52) U.S. Cl.
CPC .............. *C07K 16/18* (2013.01); *C07K 16/28* (2013.01); *C07K 16/30* (2013.01); *G01N 33/6872* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/565* (2013.01); *C07K 2317/73* (2013.01); *C07K 2317/92* (2013.01); *G01N 2333/4703* (2013.01)

(58) Field of Classification Search
CPC ........ C07K 16/18; C07K 16/28; C07K 16/30; C07K 2317/21; C07K 2317/24; C07K 2317/33; C07K 2317/34; C07K 2317/54; C07K 2317/565; C07K 2317/73; G01N 33/6872; G01N 2333/4703; A61K 2039/505

See application file for complete search history.

(56) References Cited

U.S. PATENT DOCUMENTS

| 2012/0004117 A1 | 1/2012 | Aburatani et al. |
| 2013/0178533 A1 | 7/2013 | Lee et al. |

FOREIGN PATENT DOCUMENTS

| KR | 2010/0019670 A | 2/2010 |
| KR | 2012/0023524 A | 3/2012 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Kwon et al., "Prevention and therapy of hepatocellular carcinoma by vaccination with TM4SF5 epitope-CpG-DNA-liposome complex without carriers," PLoS One. 7(3):e33121 (p. 1-13) (2012).
Lee et al., "The extracellular loop 2 of TM4SF5 inhibits integrin alpha2 on hepatocytes under collagen type I environment," Carcinogenesis. 30(11):1872-9 (2009).
NCBI Accession No. AAD25025.1. (Sep. 21, 2000) (9 pages).
International Search Report for International Application No. PCT/KR2014/001567, mailed on Jun. 2, 2014 (6 pages).

* cited by examiner

*Primary Examiner* — Robert Landsman
(74) *Attorney, Agent, or Firm* — Clark & Elbing LLP; Susan M. Michaud

(57) ABSTRACT

The present invention provides an antibody or antigen binding fragment thereof, that binds to TM4SF5, and uses thereof. The antibody of this invention inhibits the growth, metastasis and invasion of cancer cells expressing TM4SF5 by binding to a tumor-specific antigen, TM4SF5, with high affinity, and therefore can be used to diagnose, prevent or treat various cancers expressing TM4SF5.

13 Claims, 31 Drawing Sheets

FIG. 4A
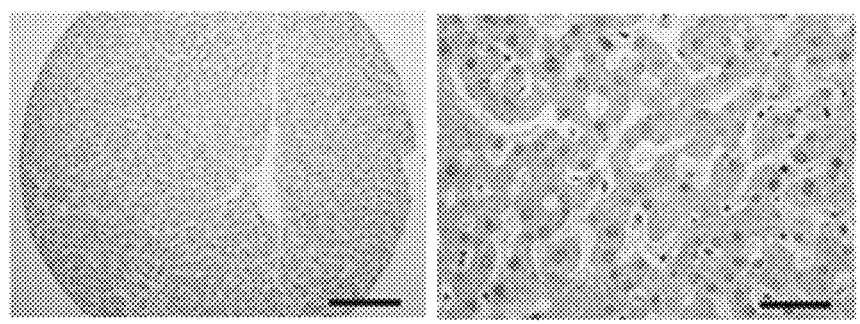
FIG. 4B
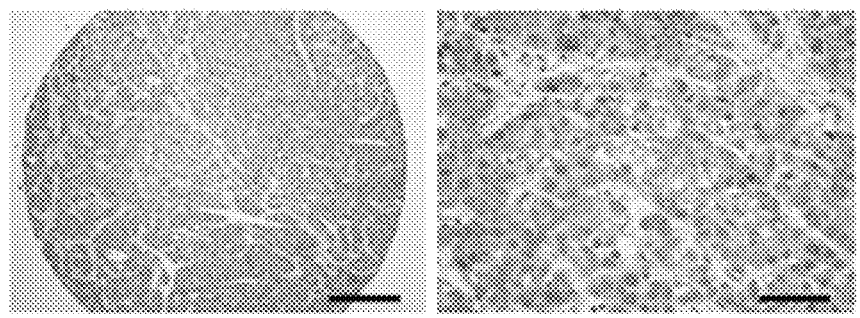
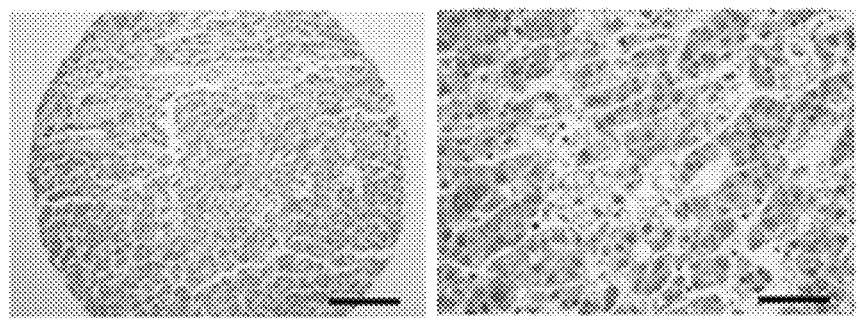
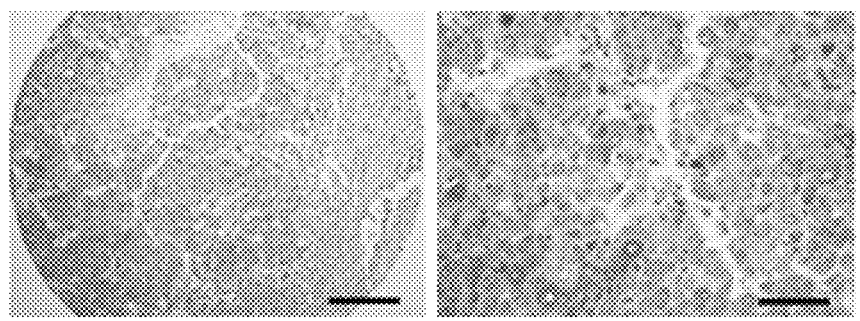

FIG. 8A
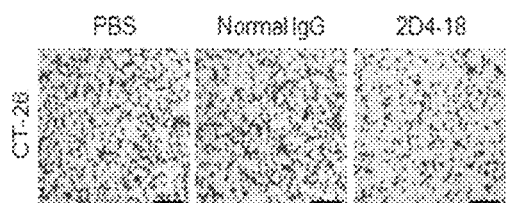
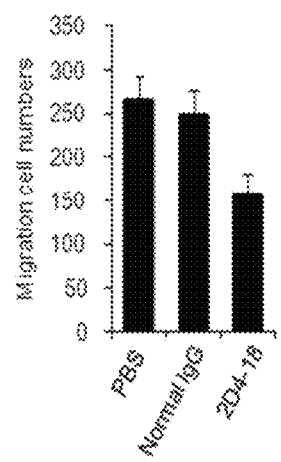
FIG. 8B
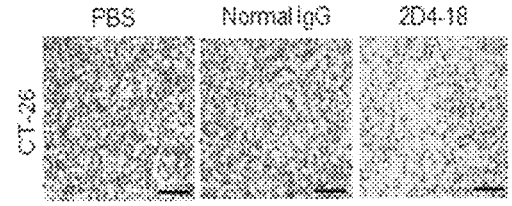
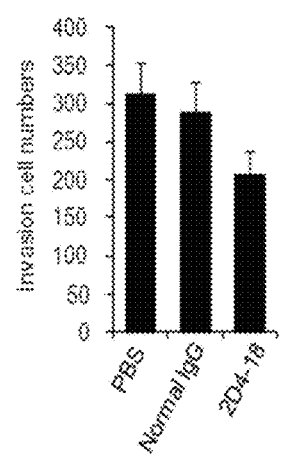
FIG. 8C
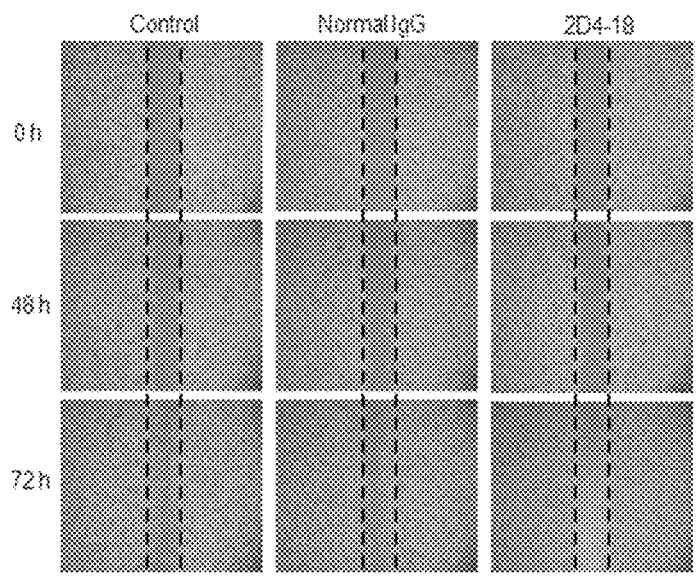

FIG. 15A

2D4-18 variable domain of heavy chain (V$_H$)

```
gggagacttagtgaagcctggagggtccctgaaactctcctgtgcagcctctggattcact
  G  D  L  V  K  P  G  G  S  L  K  L  S  C  A  A  S  G  F  T
tcagtagctatggcatgtcttgggttcgccagactccagacaagaggctggagtgggtc
 F  S  S  Y  G  M  S  W  V  R  Q  T  P  D  K  R  L  E  W  V
gcaaccattagtagtggtggtggttacacctactatccagacagtgtgaaggggcgattc
 A  T  I  S  S  G  G  G  Y  T  Y  Y  P  D  S  V  K  G  R  F
accatctccagagacaatgccaagaacaccctgtacctgcaaatgcgcagtctgaagtct
 T  I  S  R  D  N  A  K  N  T  L  Y  L  Q  M  R  S  L  K  S
gaggacacagccatgtattactgtgcaagacatgagggctttacgacgtactactttgac
 E  D  T  A  M  Y  Y  C  A  R  H  E  G  F  T  T  Y  Y  F  D
tactggggccaaggcaccactctcacagtctcctcag
 Y  W  G  Q  G  T  T  L  T  V  S  S
```

FIG. 15B

2D4-18 variable domain of light chain kappa (V$_L$)

```
ctctcctgcctgtcagtcttggagatcaagcctccatctcttgcagatctagtcagagc
  L  S  L  P  V  S  L  G  D  Q  A  S  I  S  C  R  S  S  Q  S
attttacatagttctggaaacacctatttagaatggtacctgcagaaaccaggccagtct
 I  L  H  S  S  G  N  T  Y  L  E  W  Y  L  Q  K  P  G  Q  S
ccaaagctcctgatctacaaagtttccaaccgattttctggggtcccagacaggttcagt
 P  K  L  L  I  Y  K  V  S  N  R  F  S  G  V  P  D  R  F  S
ggcagtggatcagggacagatttcacactcaagatcagcagagtggaggctgaggatctg
 G  S  G  S  G  T  D  F  T  L  K  I  S  R  V  E  A  E  D  L
ggagtttattactgctttcaaggttcacatgttccattcacgttcggctcggggacaaag
 G  V  Y  Y  C  F  Q  G  S  H  V  P  F  T  F  G  S  G  T  K
ttggaaataaaacggg
 L  E  I  K  R
```

FIG. 16A

2D4-18(1) variable domain of heavy chain (V_H)

```
caggtccagctggagcagtctgg
 Q  V  Q  L  E  Q  S  G gggacttagtgaagcctggagggtccctgaaactctcctgtgcagcctctggattcact
 G  D  L  V  K  P  G  G  S  L  K  L  S  C  A  A  S  G  F  T
ttcagtagctatggcatgtcttgggttcgccagactccagacaagaggctggagtgggtc
 F  S  S  Y  G  M  S  W  V  R  Q  T  P  D  K  R  L  E  W  V
gcaaccattagtagtggtggtggttacacctactatccagacagtgtgaaggggcgattc
 A  T  I  S  S  G  G  Y  T  Y  Y  P  D  S  V  K  G  R  F
accatctccagagacaatgccaagaacaccctgtacctgcaaatgcgcagtctgaagtct
 T  I  S  R  D  N  A  K  N  T  L  Y  L  Q  M  R  S  L  K  S
gaggacacagccatgtattactgtgcaagacatgagggcttcacgacgtactactttgac
 E  D  T  A  M  Y  Y  C  A  R  H  E  G  F  T  T  Y  Y  F  D
tactggggccaaggcaccactctcacagtctcctcag
 Y  W  G  Q  G  T  T  L  T  V  S  S
```

FIG. 16B

2D4-18(1) variable domain of light chain kappa (V_L)

```
gatattgtgatgacccagtctcca
 D  I  V  M  T  Q  S  P
ctctccctgcctgtcagtcttggagatcaagcctccatctcttgcagatctagtcagagc
 L  S  L  P  V  S  L  G  D  Q  A  S  I  S  C  R  S  S  Q  S
atttacatagttctggaaacacctatttagaatggtacctgcagaaaccaggccagtct
 I  L  H  S  G  N  T  Y  L  E  W  Y  L  Q  K  P  G  Q  S
ccaaagctcctgatctacaaagtttccaaccgatttctggggtcccagacaggttcagt
 P  K  L  L  I  Y  K  V  S  N  R  F  S  G  V  P  D  R  F  S
ggcagtggatcaggacagatttcacactcaagatcagcagagtggaggctgaggatctg
 G  S  G  S  G  T  D  F  T  L  K  I  S  R  V  E  A  E  D  L
ggagtttattactgctttcaaggttcacatgttccattcacgttcggctcggggacaaag
 G  V  Y  Y  C  F  Q  G  S  H  V  P  F  T  F  G  S  G  T  K
ttggaaataaaacggg
 L  E  I  K  R
```

ANTIBODIES AGAINST TM4SF5 AND METHODS OF USE THEREOF

CROSS-REFERENCE TO RELATED APPLICATIONS

This application is a National Phase of International Application filed Feb. 26, 2014, which claims the benefit of Korean Patent Application No. 2013-0020547, filed Feb. 26, 2013, the entire contents of which are incorporated by reference herein.

BACKGROUND OF THE INVENTION

Field of the Invention

The present invention relates to an antibody or antigen binding fragment thereof, that binds to TM4SF5 (transmembrane 4 superfamily member 5 protein), a nucleic acid molecule encoding thereof, a recombinant vector, a transformant and a preparation method of the antibody therefrom, and uses of the antibody.

Description of the Related Art

The mRNA expression of TM4SF5 (transmembrane 4 superfamily member 5 protein) in human cancer is prevalently observed in pancreatic cancer, soft tissue sarcoma, gastric cancer, carcinoma of the papilla vateri, and colon cancer (Muller-Pillasch F, et al. *Gene* 208, 25-30(1998)). TM4SF5 plays an important role in hepatocellular carcinoma (HCC) formation by induced morphological elongation and epithelial-mesenchymal transition, and caused abnormal cell growth in multilayers in vitro and tumor formation in vivo (Lee S A, et al. *J Clin Invest* 118, 1354-1366(2008); Lekishvili T, et al. *J Cell Sci* 121, 685-694(2008)). It is reported that TM4SF5 expression-induced uncontrolled cell proliferation and angiogenesis was provoked by inhibition of integrin $\alpha 2$ function in collagen type I environment by extracellular interaction between TM4SF5 and integrin $\alpha 2$ (Lee S A, et al. *Carcinogenesis* 30, 1872-1879(2009)). A synthetic inhibitor targeting TM4SF5, 4'-(p-toluenesulfonyl-amido)-4-hydroxychalcone (TSAHC), has been shown to inhibit HCC growth and metastasis formation in vitro and in vivo (Lee S A, et al. *Hepatology* 49, 1316-1325(2009)). Therefore, a role for the TM4SF5 in HCC formation represents a novel molecular target for the clinical development of HCC therapeutics.

HCC is one of the most common cancers globally, and widespread especially in Asia and sub-Saharan Africa. It is reported that the development of most HCC is a multistep process including dysplastic nodule, early HCC, well-differentiated HCC, and moderately and poorly differentiated HCCs (Forner A, et al. *Lancet* 379, 1245-1255(2012)).

Colon cancer is the third most common cancer in the world, and it is more common in developed countries than undeveloped countries. The most commonly mutated genes in colon cancer are APC, β-catenin, AXIN1, AXIN2, TCF7L2, or NKD1 which are involved in the Wnt-APC-β-catenin signaling pathway (Korinek V, et al. *Science* 275, 1784-1787(1997); Khan N P, et al. *Mol Cell Biochem* 355, 149-155(2011); Folsom A R, et al. *Diabetes Care* 31, 905-909(2008); Guo J, et al. *PLoS One* 4, e7982(2009)).

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventor has made intensive researches to develop antibodies for diagnosing, preventing and treating cancers. As a result, the present inventor has prepared a novel antibody and its antigen binding fragment that binds to a tumor-specific antigen, TM4SF5, with a high affinity, and demonstrated excellent inhibitory effects of the antibody on the growth, metastasis and invasion of cancer cells.

Accordingly, it is an object of this invention to provide an antibody or antigen binding fragment thereof, that binds to TM4SF5.

It is another object of this invention to provide an antibody or antigen binding fragment thereof that binds to TM4SF5, comprising CDRs of an antibody produced from a hybridoma cell.

It is another object of this invention to provide a hybridoma cell line producing the antibody.

It is another object of this invention to provide a nucleic acid molecule encoding a heavy chain variable domain of the antibody or antigen binding fragment thereof.

It is yet another object of this invention to provide a nucleic acid molecule encoding a light chain variable domain of the antibody or antigen binding fragment thereof.

It is still another object of this invention to provide a recombinant vector comprising the nucleic acid molecule.

It is a further object of this invention to provide a host cell comprising the recombinant vector.

It is a still further object of the invention to provide a method for preparing the antibody or antigen binding fragment thereof.

It is an additional object of this invention to provide a method for identifying or detecting the presence of TM4SF5 protein in a sample.

It is another object of this invention to provide a pharmaceutical composition for preventing or treating a cancer.

It is yet another object of the invention to provide a kit for detecting TM4SF5 protein.

It is a further object of the invention to provide a method for preventing or treating a cancer.

Other objects and advantages of the present invention will become apparent from the detailed description to follow taken in conjugation with the appended claims and drawings.

BRIEF DESCRIPTION OF THE DRAWINGS

(FIG. 1A) Four BALB/c mice were immunized i.p. with hTM4SF5 peptide. The sera were collected, and the total IgG were assayed using an ELISA kit. (FIG. 1B) ELISA results from the initial screening of a cell-fusion experiment using splenocytes of hTM4SF5 peptide immunized mice. (FIG. 1C) Six hybridomas from FIG. 1B (arrow) were selected for the production of monoclonal antibody following subcloning by limiting dilution method. (FIG. 1D) The six hybridomas from FIG. 1C (arrow) were injected into i.p. cavity to generate ascites in BALB/c mice. The ascites were screened by ELISA to detect hybridomas secreting specific antibodies against hTM4SF5 peptide. (FIG. 1E) The 2D4-18 hybridoma clone was injected into i.p. cavity to generate ascites in 7 BALB/c mice. The sera (FIG. 1A), hybridoma culture supernatants (FIG. 1B and FIG. 1C) and ascites (FIG. 1D and FIG. 1E)

were collected, and titers and amounts of the peptide-specific total IgG were assayed with an ELISA kit.

Figure 2:
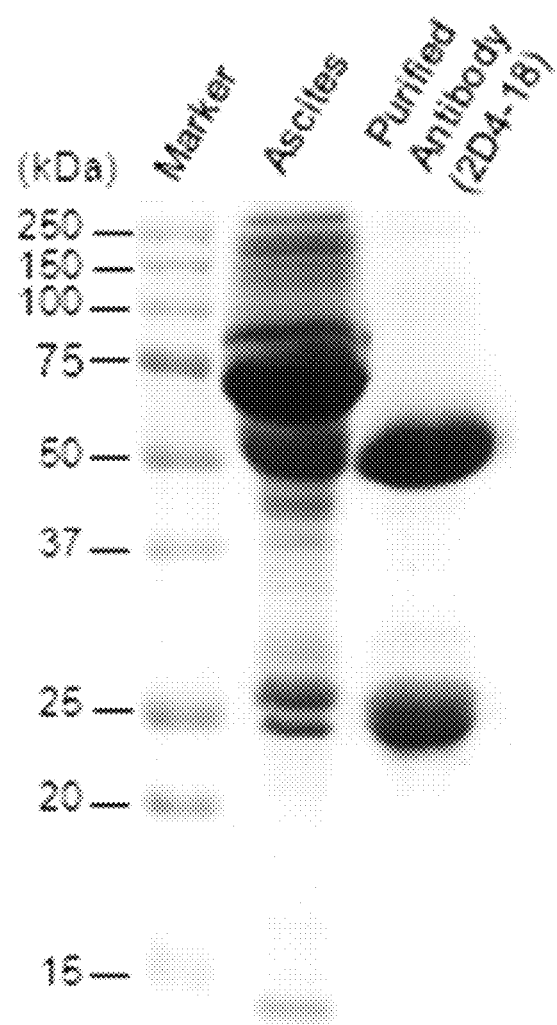

FIG. 2 represents purification of anti-TM4SF5 monoclonal antibody 2D4-18 from ascites of mice injected with mouse hybridoma cell line 2D4-18. Marker, ascites, purified monoclonal antibody was separated by SDS-PAGE and stained with Coomassie brilliant blue.

Figure 3A:
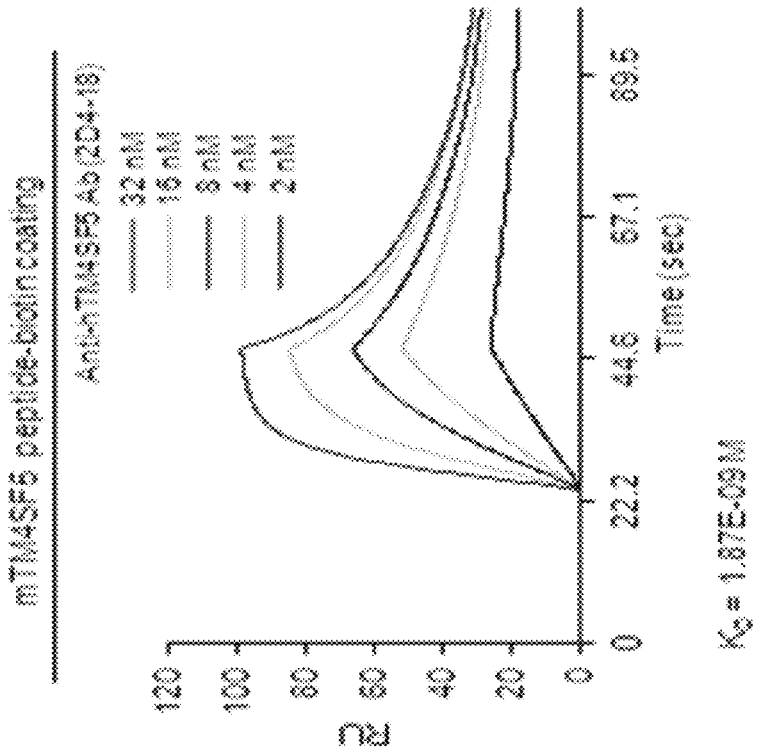
Figure 3B:
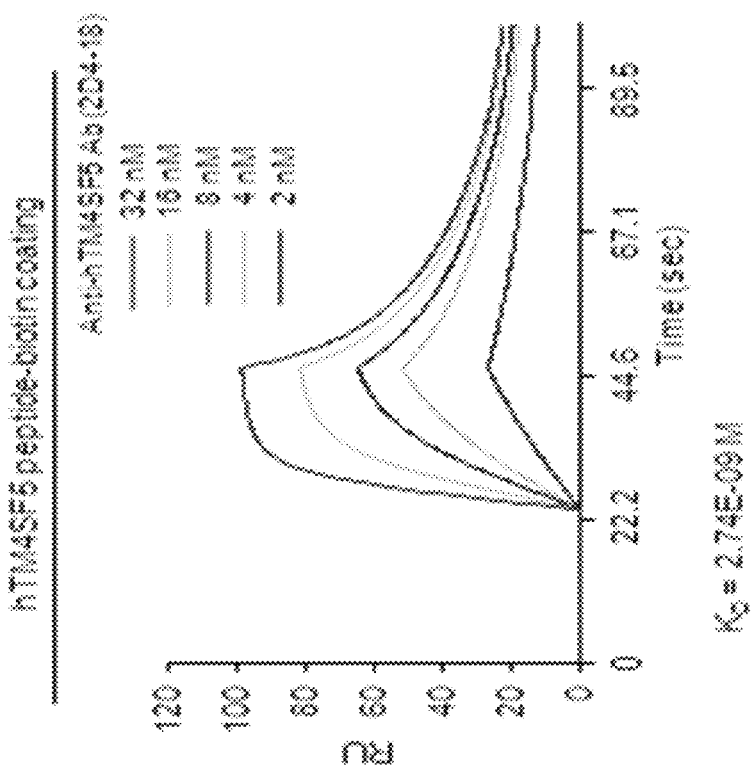

FIG. 3A-B represents binding affinity of anti-TM4SF5 monoclonal antibody 2D4-18. FIG. 3A: Binding affinity to hTM4SF5, FIG. 3B: Binding affinity to mTM4SF5.

FIG. 4A-B represents expression of TM4SF5 in HCC tissues. FIG. 4A: Normal liver tissue, FIG. 4B: Examples of HCC tissues with >75%, 74-50%, and 49-11% TM4SF5 expression of tumors present. Scale bar=200 µm (left), 50 µm (right).

Figure 5A:
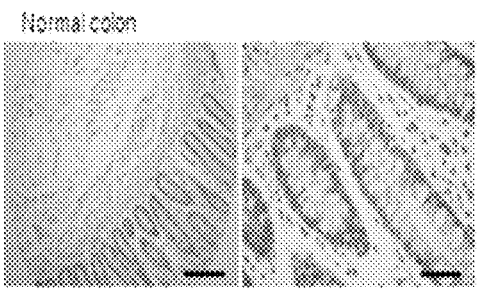
Figure 5B:
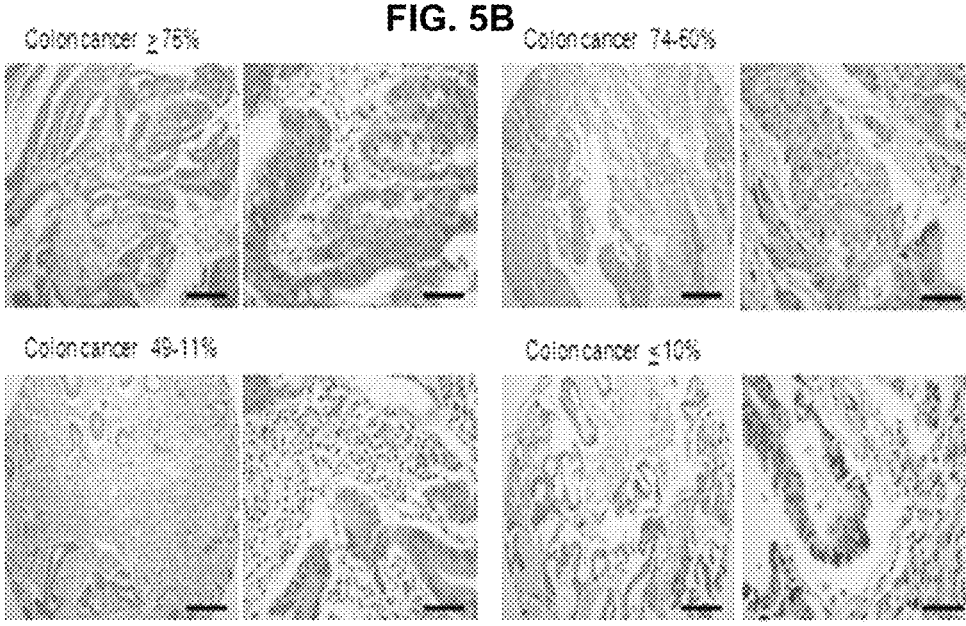
Figure 5C:
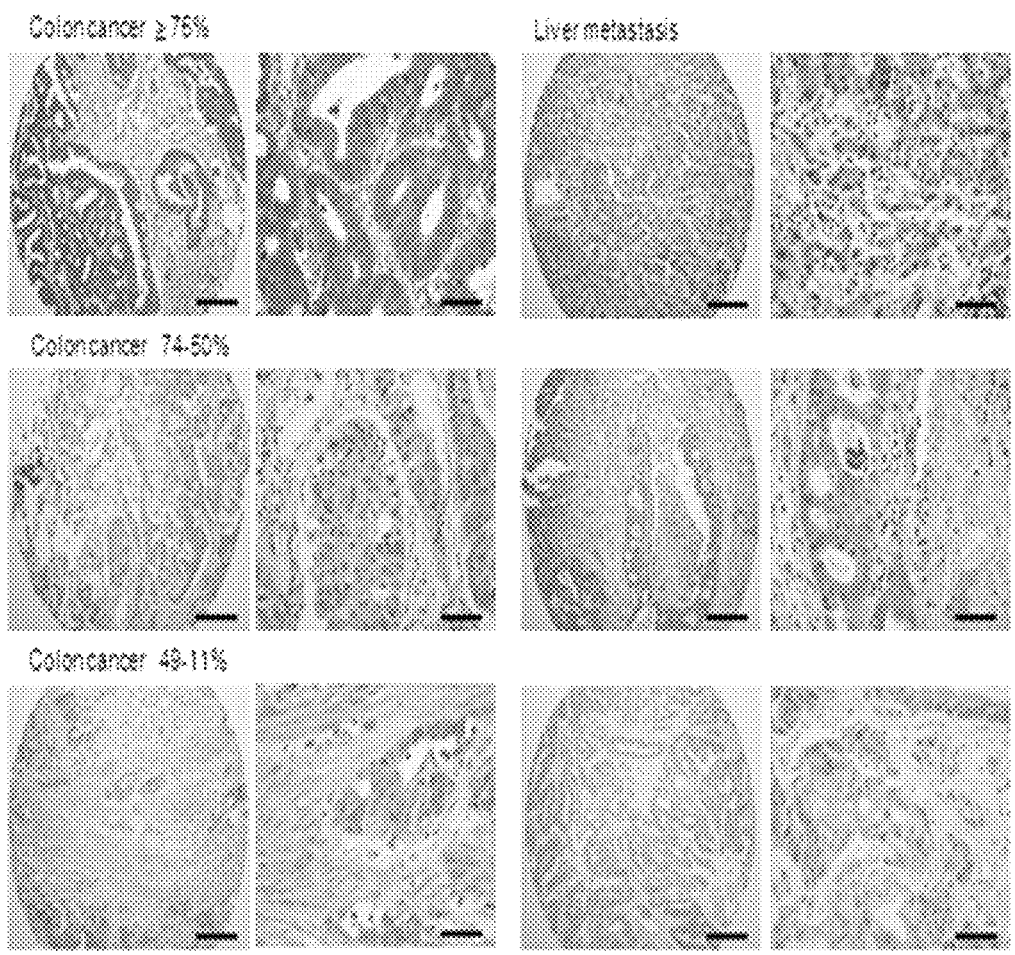

FIG. 5A-C represent expression of TM4SF5 in colon cancer tissues. FIG. 5A: Normal colon tissue, FIG. 5B: Examples of colon cancer tissues with >75%, 74-50%, 49-11%, and <10% TM4SF5 expression of tumors present, FIG. 5C: Colon cancer tissues and liver metastasis tissues of three colon cancer patients with metastasized liver cancer. Scale bar=200 µm (left), 50 µm (right).

Figure 6A:
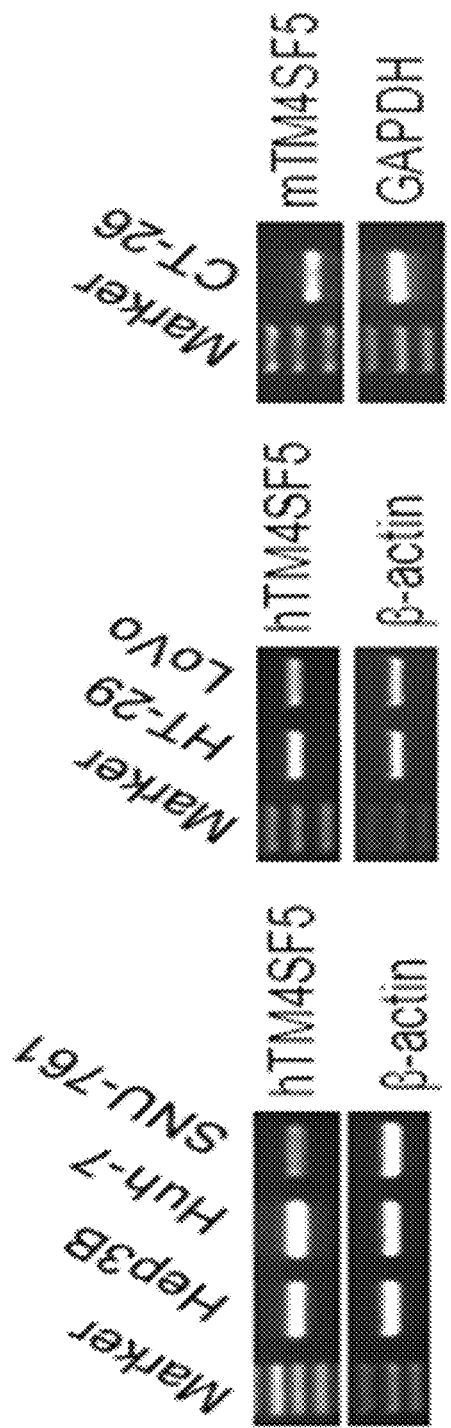
Figure 6B:
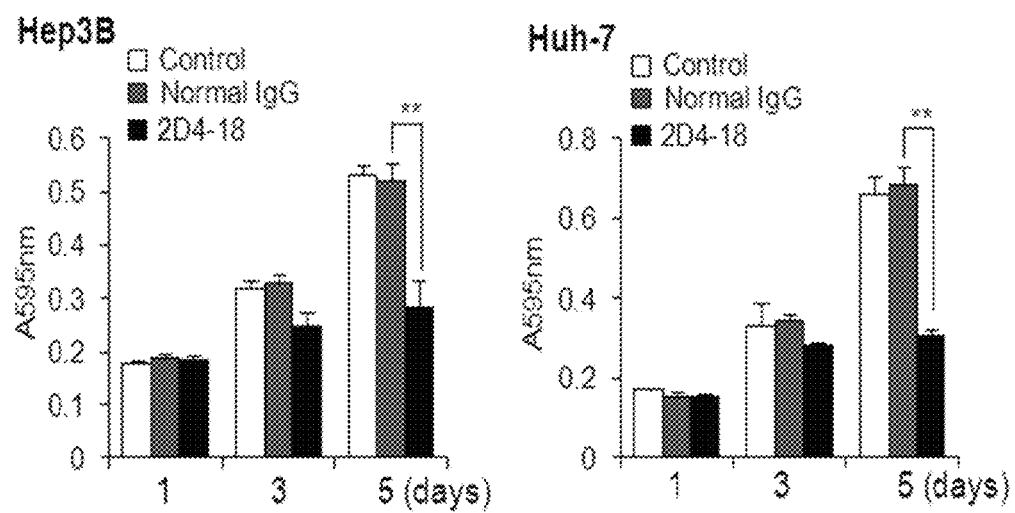
Figure 6C:
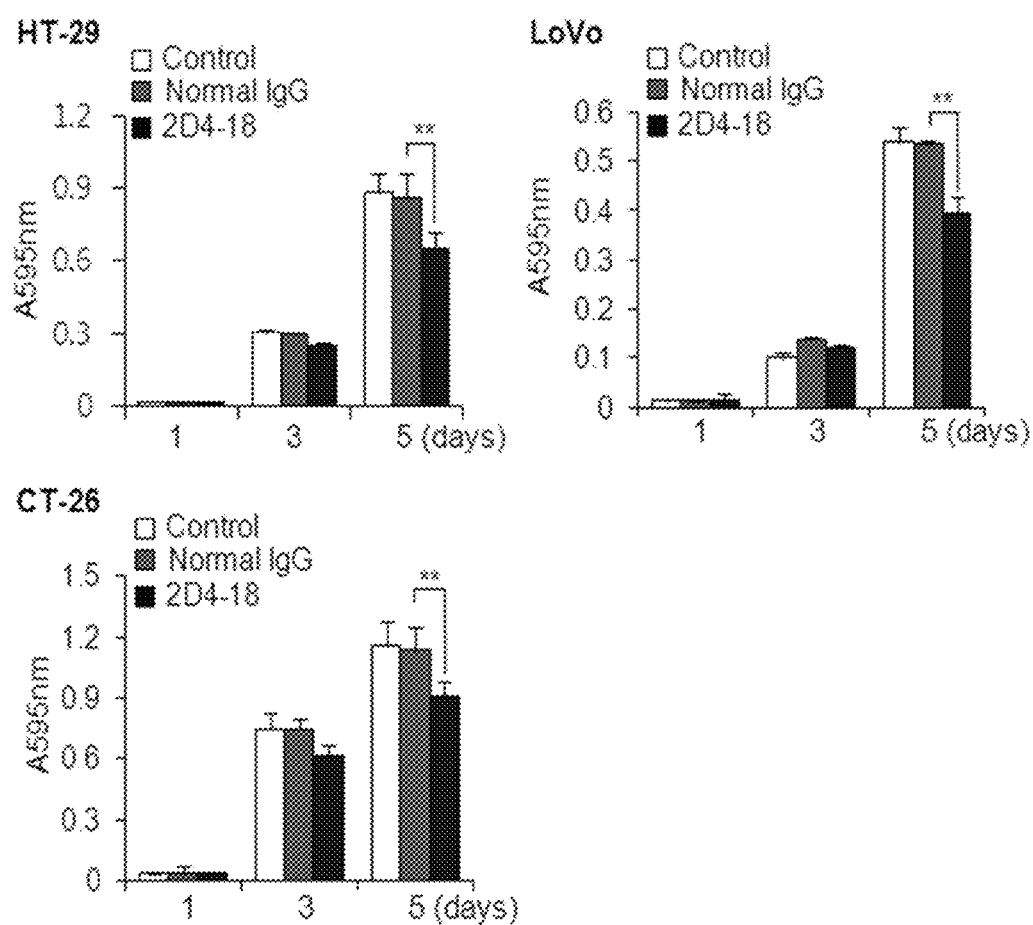

FIG. 6A-C represents inhibitory effects of anti-TM4SF5 monoclonal antibody 2D4-18 on growth of HCC cells and colon cancer cells. (FIG. 6A) Expression of TM4SF5 mRNA in the HCC cell lines and colon cancer cell lines. (FIG. 6B) Effects of anti-TM4SF5 monoclonal antibody 2D4-18 on HCC cells growth. Each bar is expressed as a Mean±SD of three experiments. P<0.01 (vs normal IgG control). (FIG. 6C) Effects of anti-TM4SF5 monoclonal antibody 2D4-18 on colon cancer cells growth. Each bar is expressed as a Mean±SD of three experiments. P<0.01 (vs normal IgG control).

Figure 7A:
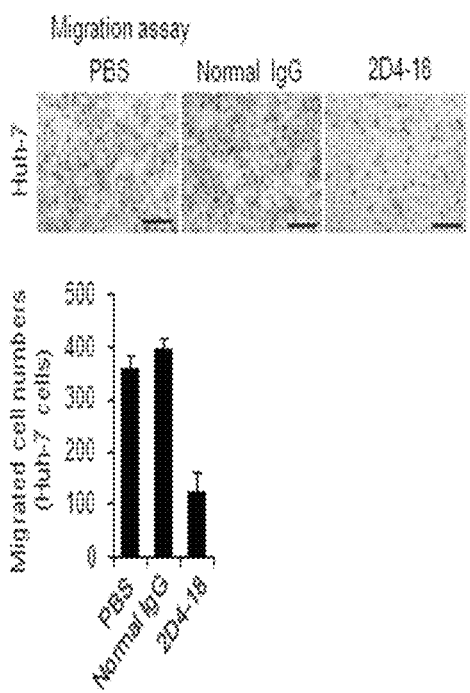
Figure 7B:
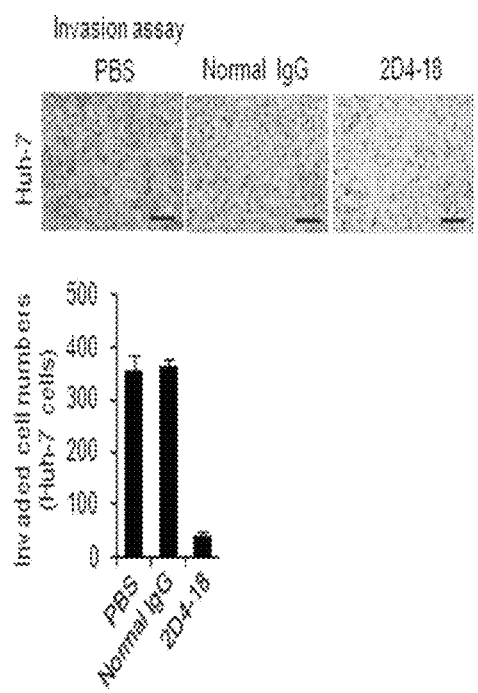
Figure 7C:
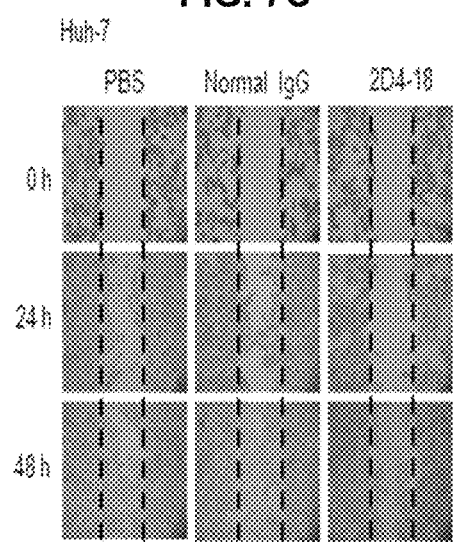

FIG. 7A-C represents effects of anti-TM4SF5 monoclonal antibody 2D4-18 on migration and invasion of HCC cells. FIG. 7A: Migration assay, FIG. 7B: Invasion assay, FIG. 7C: Wound-healing assay. Scale bar=200 µm.

FIG. 8A-C represents effects of anti-TM4SF5 monoclonal antibody 2D4-18 on migration and invasion of colon cancer cells. FIG. 8A: Migration assay, FIG. 8B: Invasion assay, FIG. 8C: Wound-healing assay. Scale bar=200 µm.

Figure 9A:
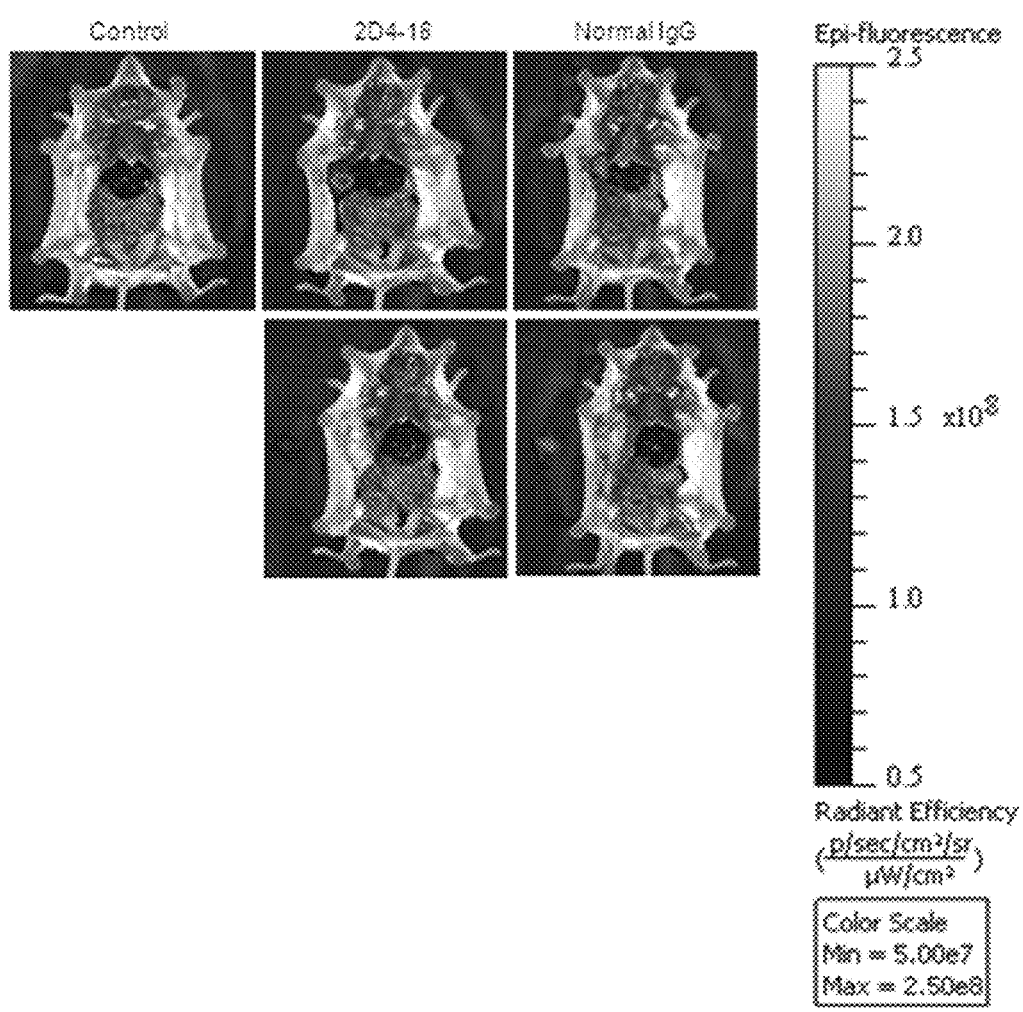
Figure 9B:
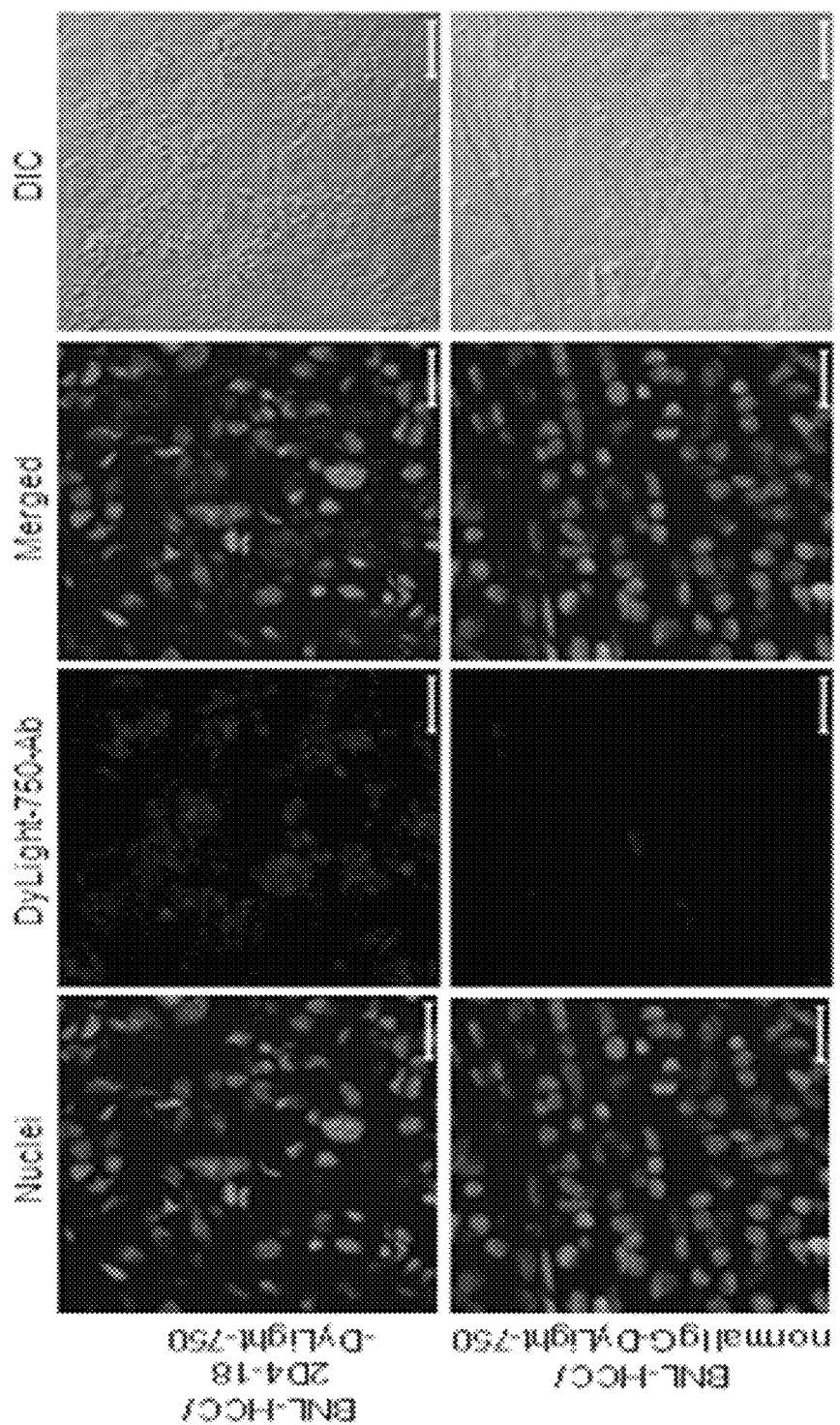

FIG. 9A-B biodistribution of anti-TM4SF5 monoclonal antibody 2D4-18 in HCC tumor tissue. (FIG. 9A) The mice were dissected and localization of the antibody in the mice was examined by using the real-time IVIS imaging system 200 (upper panel). The tumor tissues were taken out and placed on the left of the mice (lower panel). (FIG. 9B) The dissected tumor tissue was frozen and the microsection samples were analyzed by confocal microscopy. Scale bar=20 µm.

Figure 10A:
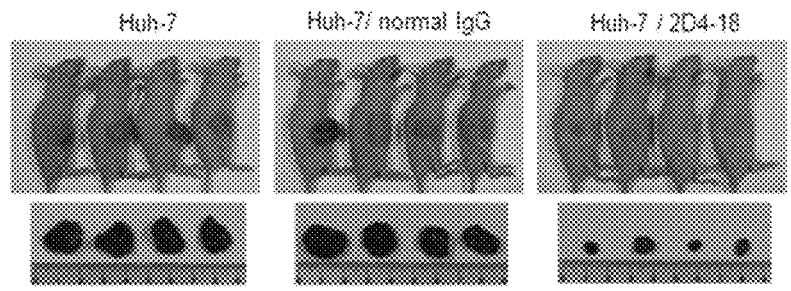
Figure 10B:
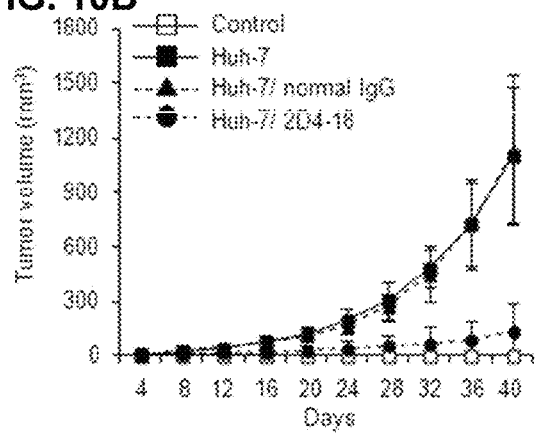
Figure 10C:
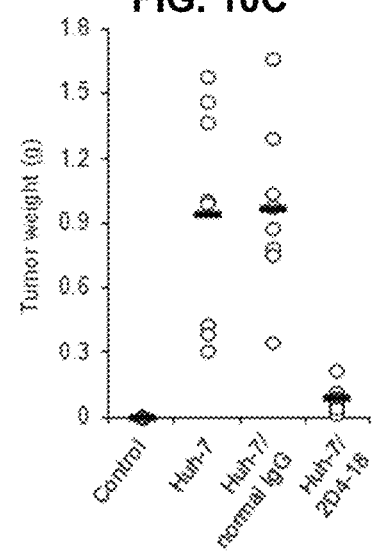
Figure 10D:
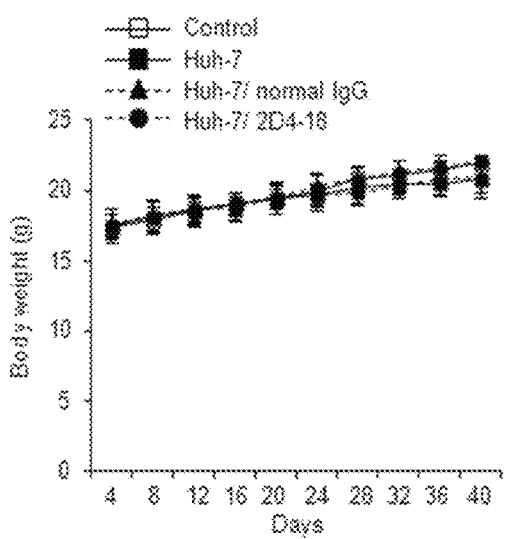
Figure 10E:
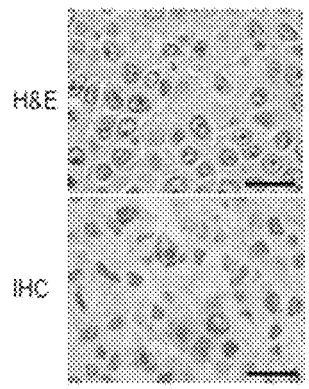

FIG. 10A-E represents therapeutic efficacy of injected anti-TM4SF5 monoclonal antibody 2D4-18 against HCC tumor growth in an xenograft mouse model. FIG. 10A: Macroscopic appearance of HCC tumor tissues, FIG. 10B: Tumor volumes, FIG. 10C: Tumor weight, FIG. 10D: Body weights, FIG. 10E: Expression of TM4SF5 in the tumor tissue. TM4SF5 positive area was expressed as brown color. Scale bar=20 µm.

Figure 11A:
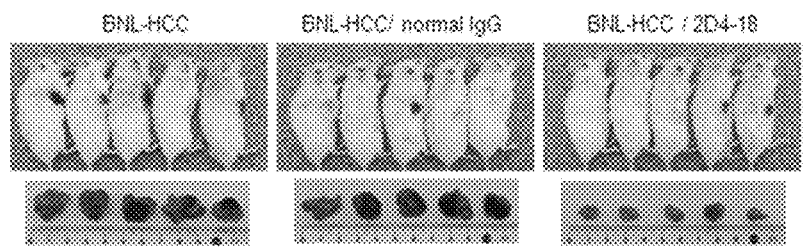
Figure 11B:
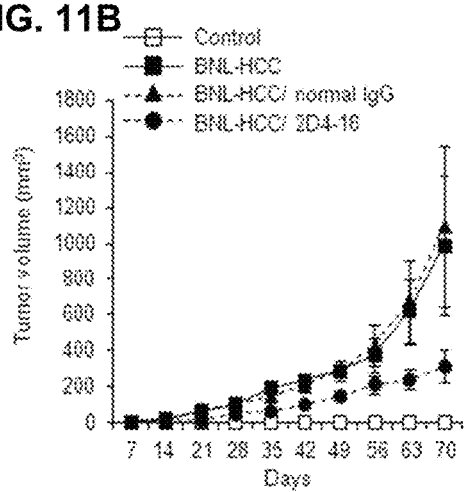
Figure 11C:
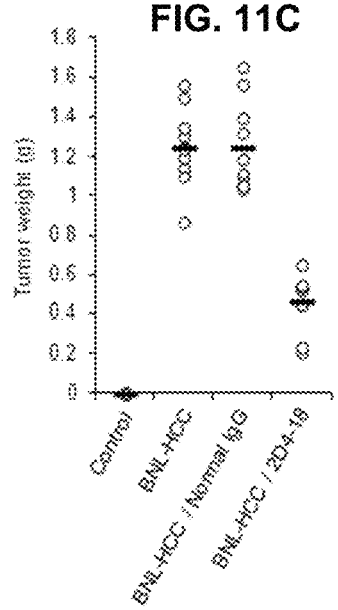
Figure 11D:
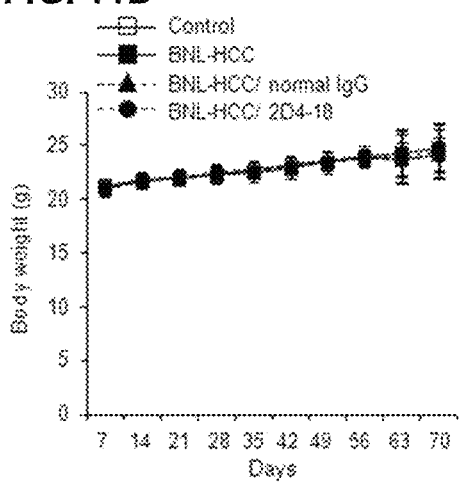
Figure 11E:
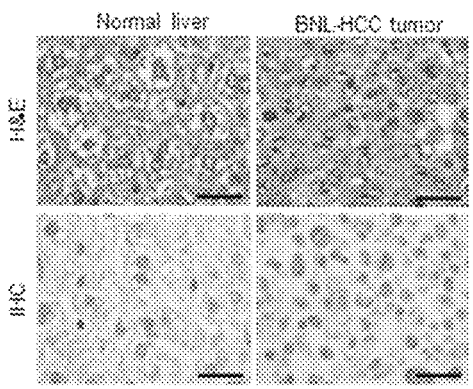

FIG. 11A-E represents therapeutic efficacy of anti-TM4SF5 monoclonal antibody 2D4-18 against HCC tumor growth in an allograft mouse model. FIG. 11A: Macroscopic appearance of HCC tumor tissues, FIG. 11B: Tumor volumes, FIG. 11C: Tumor weight, FIG. 11D: Body weights, FIG. 11E: Expression of TM4SF5 in the tumor tissue. TM4SF5 positive area was expressed as brown color. Scale bar=20 µm.

Figure 12A:
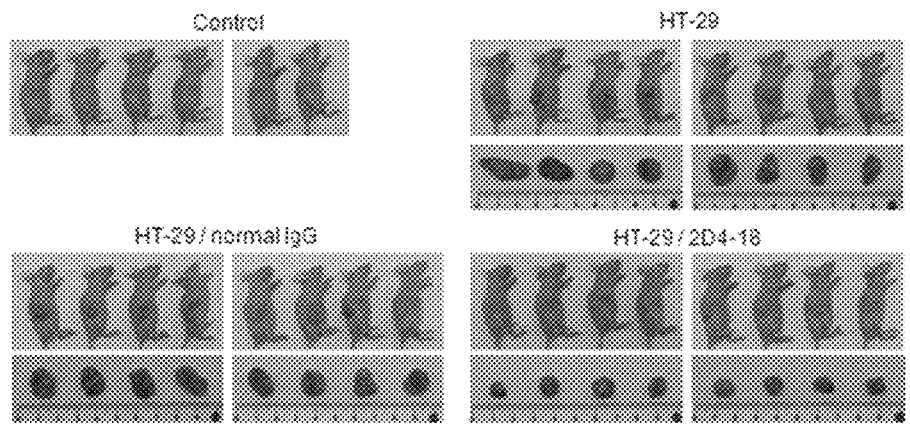
Figure 12B:
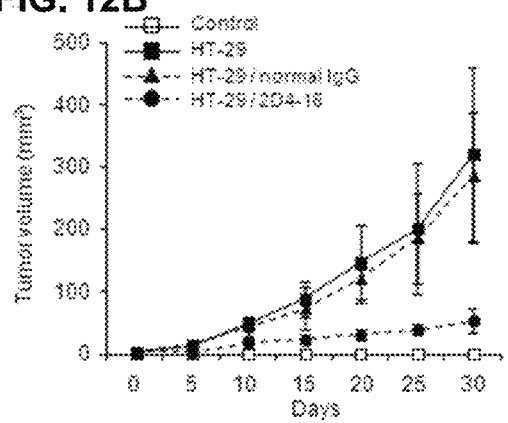
Figure 12C:
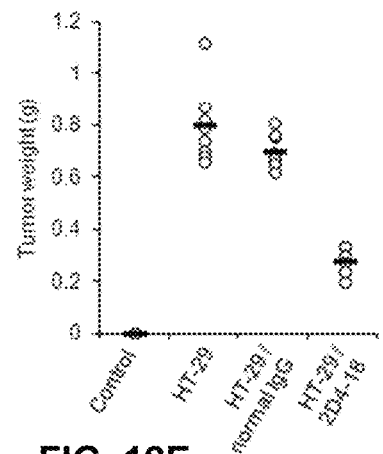
Figure 12D:
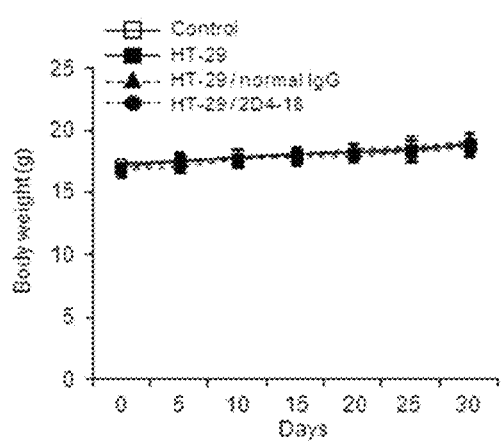
Figure 12E:
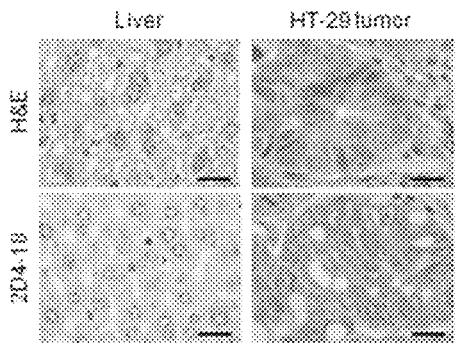

FIG. 12A-E represents therapeutic efficacy of anti-TM4SF5 monoclonal antibody 2D4-18 against colon cancer growth in an xenograft mouse model. FIG. 12A: Macroscopic appearance of colon cancer tissues, FIG. 12B: Tumor volumes, FIG. 12C: Tumor weight, FIG. 12D: Body weights, FIG. 12E: Expression of TM4SF5 in the tumor tissue. TM4SF5 positive area was expressed as brown color. Scale bar=20 µm.

Figure 13A:
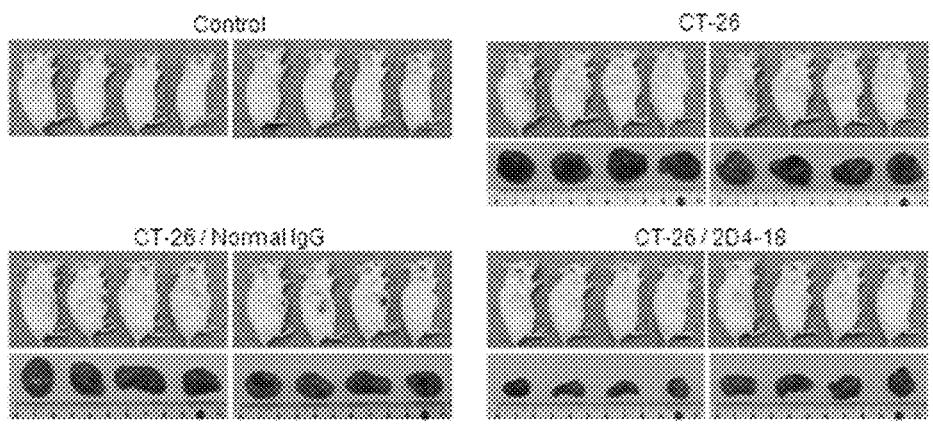
Figure 13B:
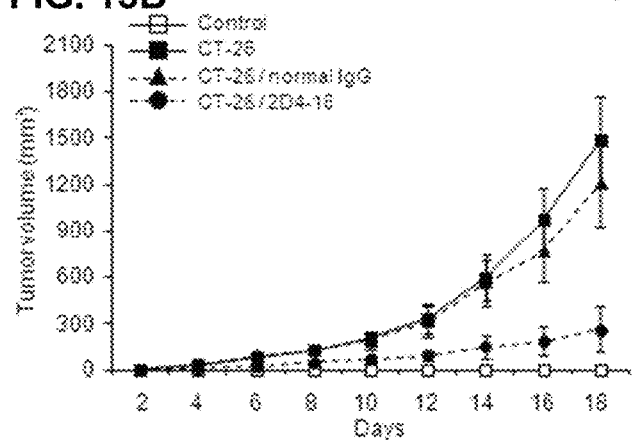
Figure 13C:
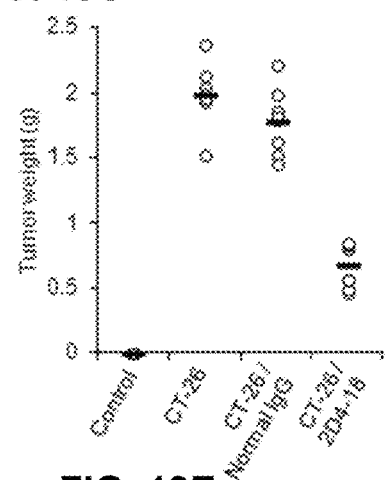
Figure 13D:
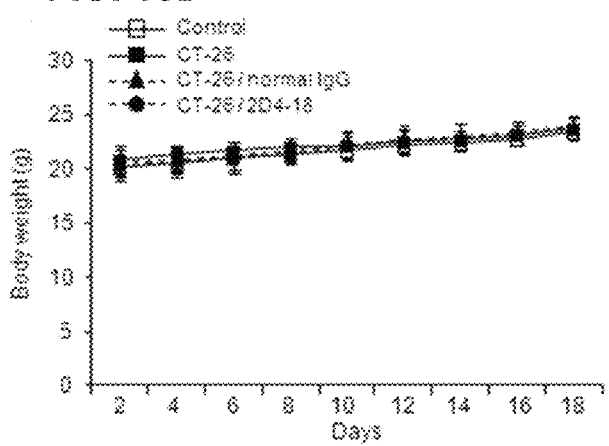
Figure 13E:
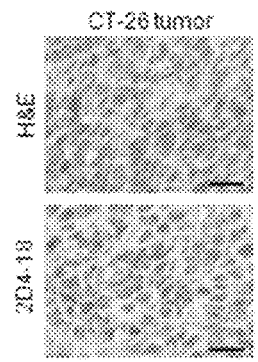

FIG. 13A-E represents therapeutic efficacy of anti-TM4SF5 monoclonal antibody 2D4-18 against colon cancer growth in an allograft mouse model. FIG. 13A: Macroscopic appearance of colon cancer tissues, FIG. 13B: Tumor volumes, FIG. 13C: Tumor weight, FIG. 13D: Body weights, FIG. 13E: Expression of TM4SF5 in the tumor tissue. TM4SF5 positive area was expressed as brown color. Scale bar=20 µm.

Figure 14A:
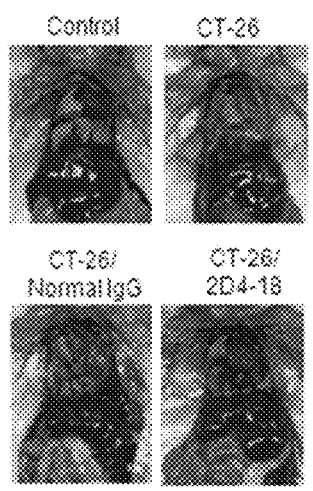
Figure 14B:
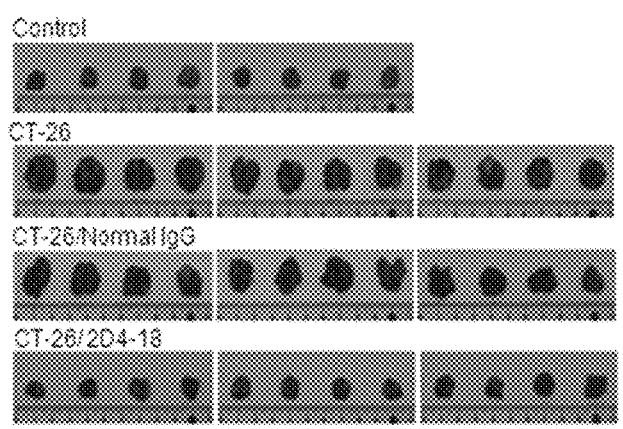
Figure 14C:
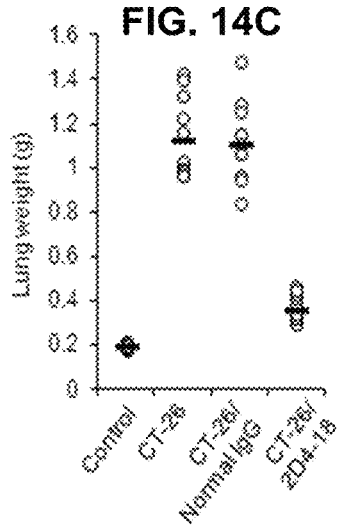
Figure 14D:
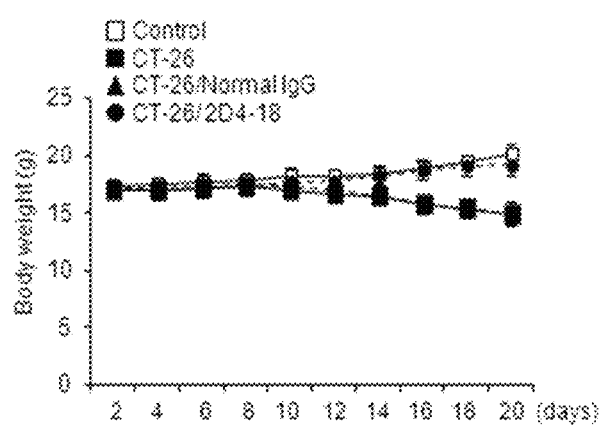

FIG. 14A-D represents the inhibition of lung metastasis by anti-TM4SF5 monoclonal antibody 2D4-18 in an allograft colon cancer model. FIG. 14A and FIG. 14B: Macroscopic appearance of lung, FIG. 14C: Lung weight, FIG. 14D: Body weights.

FIG. 15A-B represents cDNA sequences (2D4-18) for variable domains of heavy and light chains isolated from the hybridoma cell clone 2D4-18. FIG. 15A: Sequence of the heavy chain variable domain (SEQ ID NOs:25 and 27), FIG. 15B: Sequence of the light chain variable domain (SEQ ID NOs:26 and 28). Predicted amino acid sequences (SEQ ID NOs:25 and 26) are indicated under the cDNA sequences (SEQ ID NOs:27 and 28).

FIG. 16A-B represents cDNA sequences (2D4-18(1)) for variable domains of heavy and light chains isolated from the hybridoma cell clone 2D4-18. FIG. 16A: Sequence of the heavy chain variable domain (SEQ ID NOs:29 and 31), FIG. 16B: Sequence of the light chain variable domain (SEQ ID NOs:30 and 32). Predicted amino acid sequences (SEQ ID NOs:29 and 30) are indicated under the cDNA sequences (SEQ ID NOs: 31 and 32).

Figure 17A:
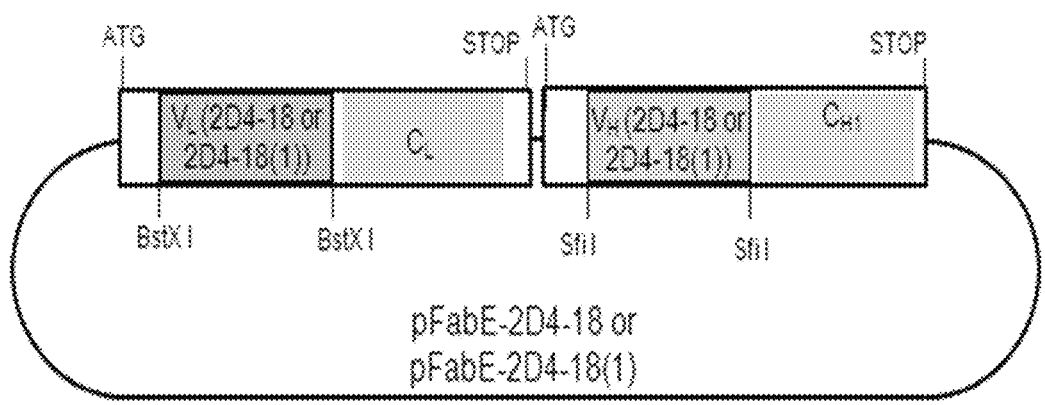
Figure 17B:
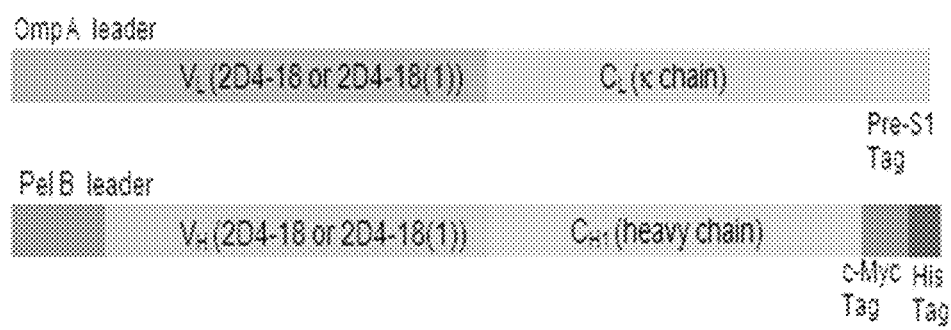

FIG. 17A-B represents a map of the expression vectors (pFabE-2D4-18 and pFabE-2D4-18 (1)) (FIG. 17A), and the predicted protein structure expressed from the expression vectors (FIG. 17B).

Figure 18A:
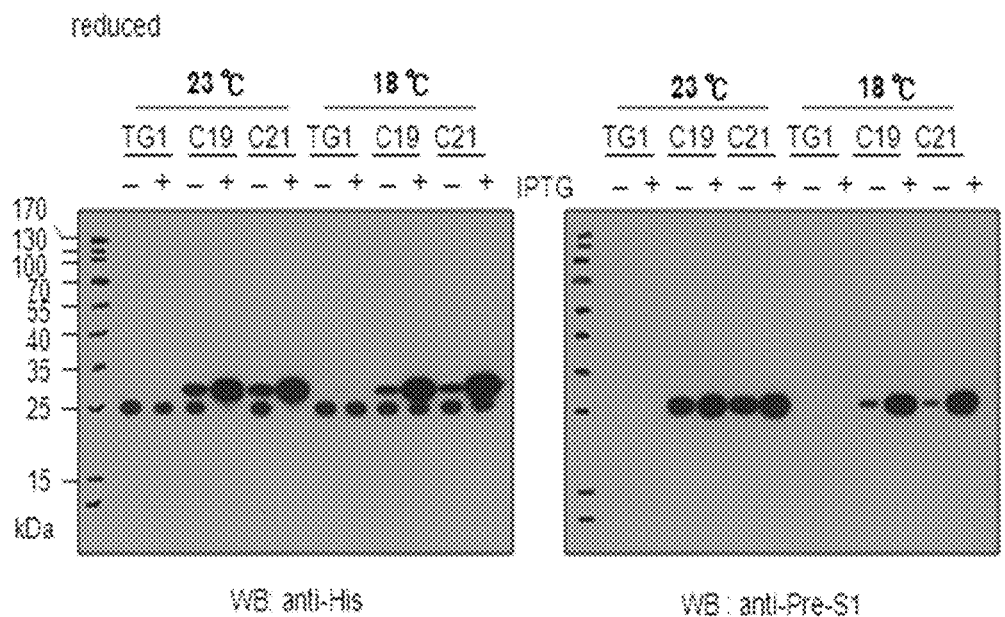
Figure 18B:
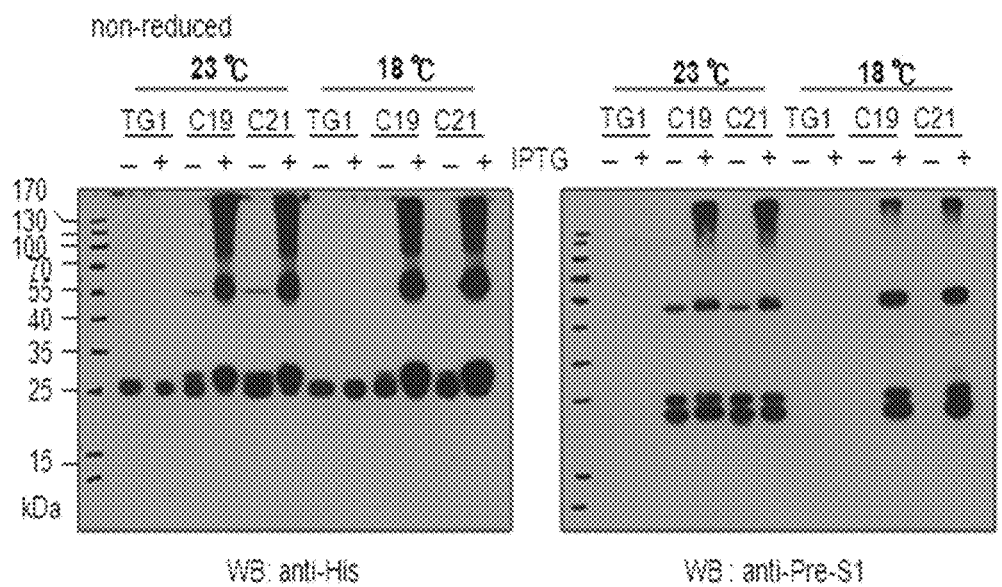

FIG. 18A-B represents the production of the recombinant Fab-2D4-18 in *E. coli* at a small scale. FIG. 18A: Reduced total cell lysates, FIG. 18B: Non-reduced total cell lysates.

Figure 19A:
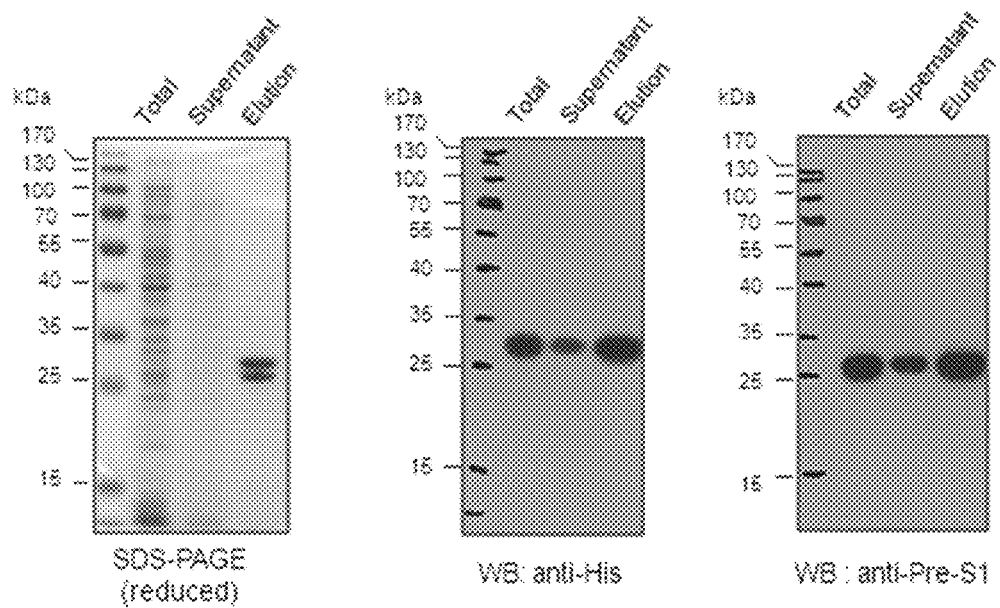
Figure 19B:
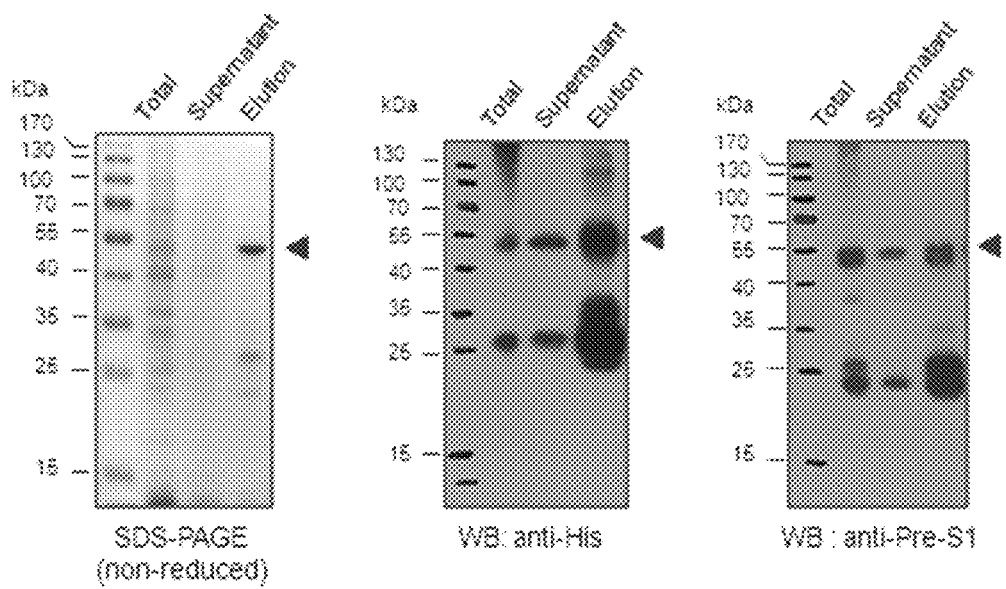

FIG. 19A-B represents the production and purification of the recombinant Fab-2D4-18 in *E. coli*. FIG. 19A: Reduced protein samples, FIG. 19B: Non-reduced protein samples.

Figure 20A:
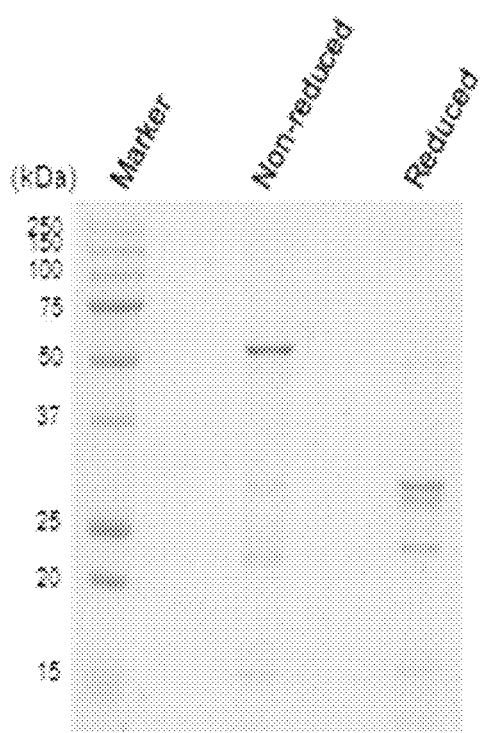
Figure 20B:
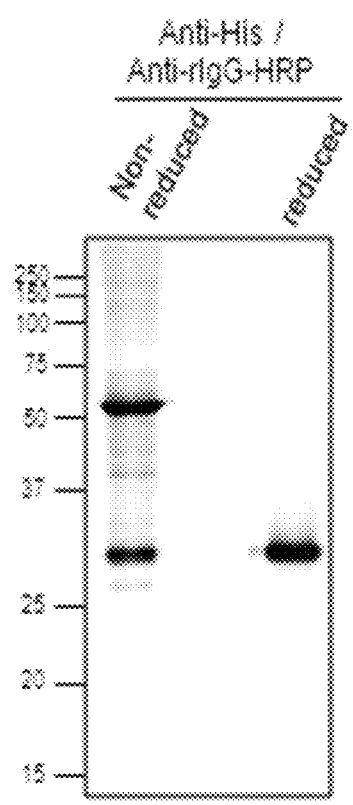

FIG. 20A-B represents the production and purification of the recombinant Fab-2D4-18(1) in *E. coli*. FIG. 20A: SDS-PAGE results, FIG. 20B: Western blot results.

Figure 21:
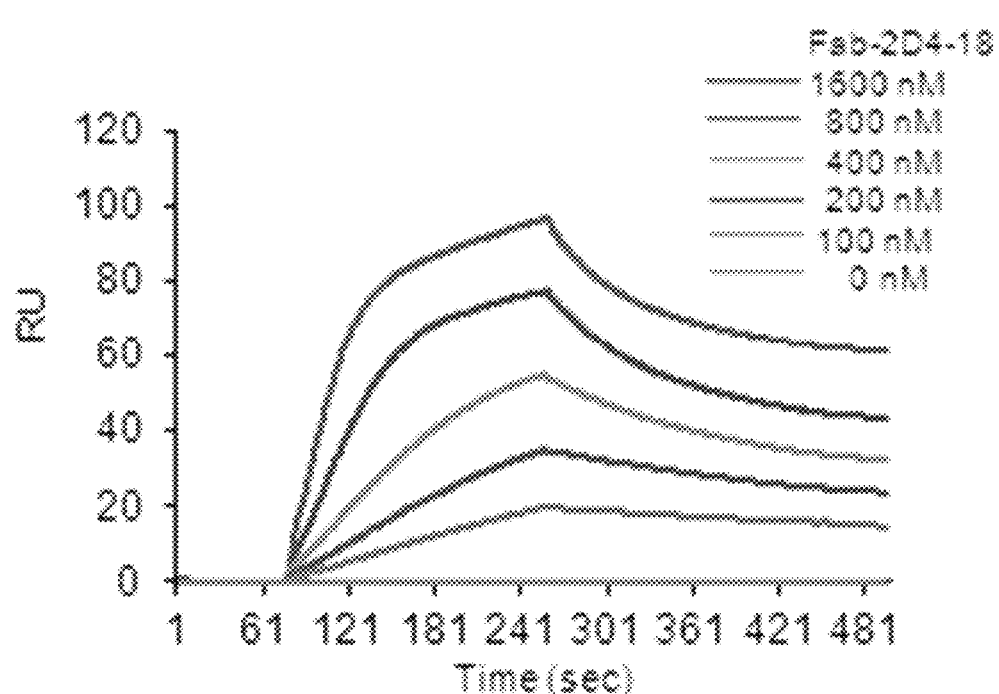

FIG. 21 represents a binding affinity of the recombinant Fab-2D4-18.

Figure 22:
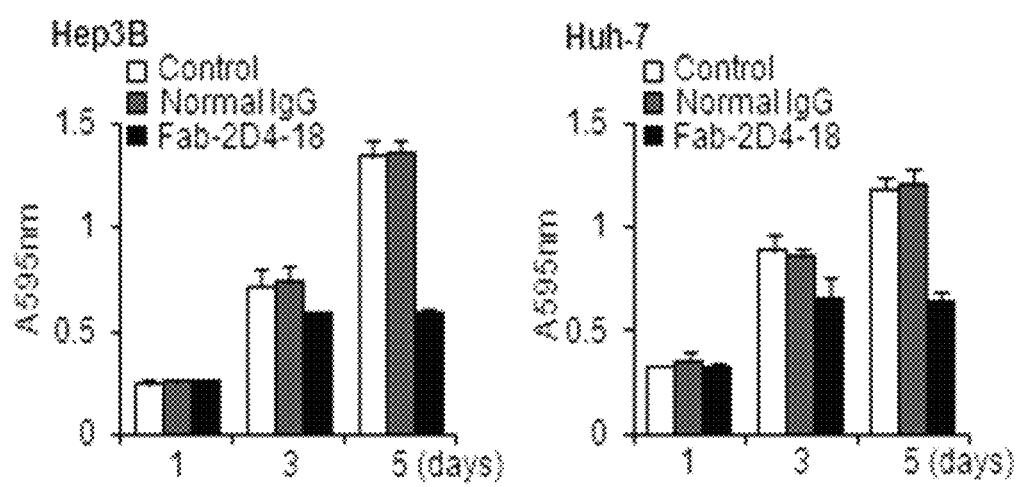

FIG. 22 represents inhibitory effects of the recombinant Fab-2D4-18 on the growth of HCC cells.

Figure 23:
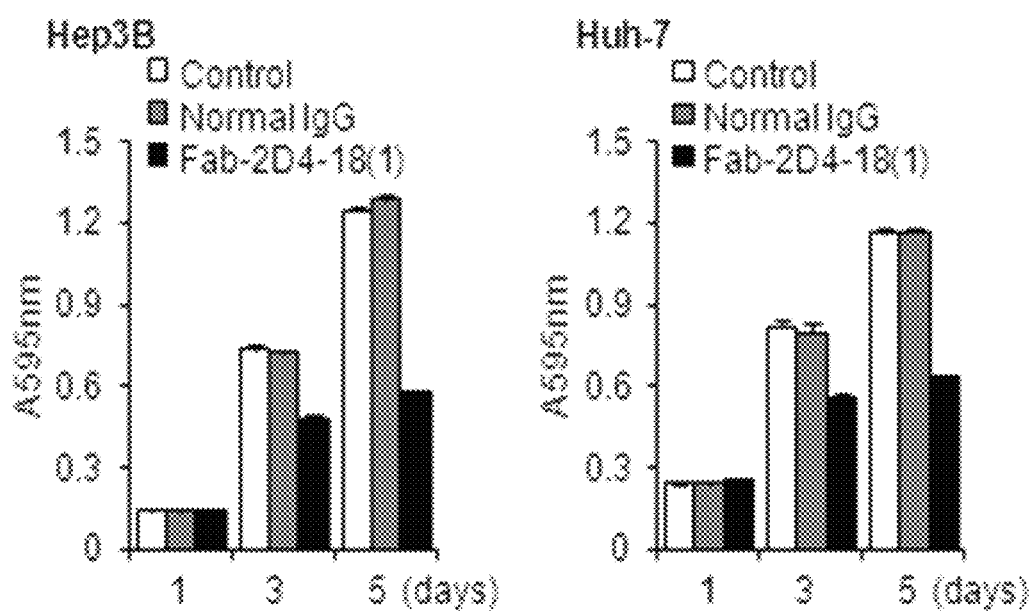

FIG. 23 represents inhibitory effects of the recombinant Fab-2D4-18(1) on the growth of HCC cells.

DETAILED DESCRIPTION OF THIS INVENTION

In one aspect of the present invention, there is provided an antibody or antigen binding fragment thereof, that binds to TM4SF5, comprising: (a) a heavy chain variable domain comprising CDRH1 of SEQ ID NO:19, CDRH2 of SEQ ID NO:20, and CDRH3 of SEQ ID NO:21; and (b) a light chain variable domain comprising CDRL1 of SEQ ID NO:22, CDRL2 of SEQ ID NO:23, and CDRL3 of SEQ ID NO:24.

The present inventor has made intensive researches to develop antibodies for diagnosing, preventing and treating cancers. As a result, the present inventor has prepared a novel antibody and its antigen binding fragment that binds to a tumor-specific antigen, TM4SF5, with a high affinity, and demonstrated excellent inhibitory effects of the antibody on the growth, metastasis and invasion of cancer cells.

The present invention will be described hereinbelow in more detail.

I. Anti-TM4SF5 Antibodies and Antigen-Binding Fragment Thereof

The antibodies of this invention have a specific binding affinity to TM4SF5.

The term "antibody" used herein refers to a TM4SF5-specific antibody which specifically binds to a particular epitope of TM4SF5, and is meant to include entire (whole) antibody as well as any antigen-binding fragment of the antibody molecule (antibody fragment).

The entire antibody includes two full-length light chains and two full-length heavy chains, and each light chain is linked to the heavy chain by disulfide bond. The heavy chain constant region includes five different isotypes (γ, μ, α, δ and ε) of which the subclass is classified into γ1, γ2, γ3, γ4, α1 and α2. The light chain constant region includes two different isotypes (κ and λ).

The antigen-binding fragment or antibody fragment refers to any antibody fragment capable of binding antigen including Fab, F(ab'), F(ab')$_2$, Fv and so on. Fab has one antigen-binding site which is composed of one variable domain from each heavy and light chain of the antibody, one constant region of light chain and the first constant region (CH$_1$) of heavy chain. Fab' is different to Fab in the sense that there is a hinge region containing one or more cysteine residues at C-terminal of CH$_1$ domain of heavy chain. F(ab')$_2$ antibody is produced by forming a disulfide bond between cysteine residues of hinge region of Fab'. Fv is a minimal antibody fragment including one variable region from each heavy and light chain and recombinant technique to prepare a Fv fragment is disclosed in PCT WO 88/10649, WO 88/106630, WO 88/07085, WO 88/07086 and WO 88/09344. Two-chain Fv is linked by non-covalent bond between one variable region of each heavy and light chain, and single-chain Fv is generally linked by covalent bond via a peptide linker between one variable region of each heavy and light chain or is directly linked to each other at C-terminal, forming a dimer such as two-chain Fv. Such antibody fragments may be obtained using a proteolytic enzymes {e.g., a whole antibody is digested with papain to produce Fab fragments, and pepsin treatment results in the production of F(ab')$_2$ fragments), and may be prepared by genetic recombination techniques.

According to an embodiment, the antibody of this invention is a form of Fab or entire antibody. In addition, the heavy chain constant region is selected from the isotypes consisting of γ, μ, α, δ or ε. In a specific embodiment, the heavy chain constant region includes γ1 (IgG1), γ3 (IgG3) and γ4 (IgG4) isotype, and in an another embodiment, the heavy chain constant region is IgG2a isotype. The light chain constant region includes κ and λ isotype. In a specific embodiment, the light chain constant region is κ isotype.

The term "heavy chain" used herein refers to both a full-length heavy chain and its part, which includes variable domain (V$_H$) containing the amino acid sequence with a variable region sequence for specifically binding to antigen and three constant domains (C$_{H1}$, C$_{H2}$ and C$_{H3}$). The term "light chain" used herein refers to both a full-length light chain and its part, which includes variable domain (V$_L$) containing the amino acid sequence with a variable region sequence for specifically binding to antigen and three constant domains (C$_L$).

The antibody or antigen binding fragment thereof of this invention comprises a heavy chain variable domain comprising CDRH1 of SEQ ID NO:19, CDRH2 of SEQ ID NO:20, and CDRH3 of SEQ ID NO:21.

The term "CDR (complementarity determining region)" used herein refers to amino acid sequences of hypervariable regions within the heavy and light chain variable domains of an immunoglobulin (Kabat et al. Sequences of Proteins of Immunological Interest, 4th Ed., U.S. Department of Health and Human Services, National Institutes of Health (1987)). Heavy chain (CDRH1, CDRH2 and CDRH3) and light chain (CDRL1, CDRL2 and CDRL3) include 3 CDRs, respectively. The CDRs provide major contact residues for binding to an antigen or an epitope.

The present antibody or its antigen-binding fragment includes variants having conservative amino acid substitutions in CDR regions. In addition, the present antibody or its antigen-binding fragment includes analogs of amino add sequences set forth in the appended Sequence Listing, which are capable of specifically recognizing TM4SF5. For example, the amino acid sequence of antibody may be altered to improve binding affinity and/or the other biological characteristics of the antibody, for example including the alterations prepared by deletion, insertion and/or substitution of amino acid residues of the antibody. Such amino acid variations may be provided on the basis of a relative similarity of amino acid side chains, e.g., hydrophobicity, hydrophilicity, charge and size. By the analysis for size, shape and type of the amino acid side chains, it could be clear that all of arginine, lysine and histidine residues are those having positive charge; alanine, glycine and serine have a similar size; phenylalanine, tryptophan and tylosin have a similar shape. Accordingly, based on these considerable factors, arginine, lysine and histidine; alanine, glysine and serine; and phenylalanine, tryptophane and tylosin may be considered to be biologically functional equivalents.

For introducing mutation, a hydropathic index of amino acids may be considered. Based on the hydrophobicity and the charge, the hydropathic index is given to each amino acid: isoleucine (+4.5); valine (+4.2); leucine (+3.8); phenylalanine (+2.8); cysteine (+2.5); methionine (+1.9); alanine (+1.8); glysine (−0.4); threonine (−0.7); serine (−0.8); tryptophane (−0.9); tylosin (−1.3); proline (−1.6); histidine (−3.2); glutamate (−3.5); glutamine (−3.5); aspartate (−3.5); asparagin (−3.5); lysine (−3.9); and arginine (−4.5).

For providing an interactive biological function of proteins, the hydropathic index of the amino acid is very important. It is well known to one of skill in the art that variations can possess a similar biological activity only where proteins are replaced with amino acids having similar hydropathic index. Where variations are intended to introduce based on the hydropathic index, the substitution is preferably performed between amino acid residues having no more than ±2 difference in hydropathic index values more preferably within ±1, much more preferably within ±0.5.

It would be also obvious to those of skill in the art that substitutions of amino acids with other amino acids having similar hydrophilicity values may result in the generation of variants having biologically equivalent activities. As disclosed in U.S. Pat. No. 4,554,101, each amino acid residue is assigned the following hydrophilicity values: arginine (+3.0); lysine (+3.0); aspartate (+3.0±1); glutamate (+3.0±1); serine (+0.3); asparagin (+0.2); glutamine (+0.2); glysine (0); threonine (−0.4); proline (−0.5±1); alanine (−0.5); histidine (−0.5); cysteine (−1.0); methionine (−1.3); valine (−1.5); leucine (−1.8); isoleucine (−1.8); tylosin (−2.3); phenylalanine (−2.5); tryptophane (−3.4).

The alteration of amino acid residues not to substantially impair protein activity is well known to one skilled in the art (H. Neurath, R. L. Hill, The Proteins, Academic Press, New York, 1979). Such amino acid alteration includes Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, but not limited to.

Considering the afore-mentioned variations having biologically equivalent activities, it could be understood that either antibody of this invention or the nucleic acid encoding the same includes substantially identical sequences to the sequences set forth in the appended Sequence Listing. The substantially identical sequences refers to those showing preferably at least 61%, more preferably at least 70%, still more preferably at least 80%, most preferably at least 90% nucleotide similarity to the sequences of the appended Sequence Listing, as measured using one of the sequence comparison algorithms. Methods of alignment of sequences for comparison are well-known in the art. Various programs and alignment algorithms are described in: Smith and Waterman, *Adv. Appl. Math.* 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44(1988); Higgins and Sharp, *CABIOS* 5: 151-3(1989); Corpet et al., *Nuc. Acids Res.* 16:10881-90 (1988); Huang et al., *Comp. Appl. BioSci* 8:155-65(1992); and Pearson et al., *Meth. MoL Biol.* 24:307-31(1994). The NCBI Basic Local Alignment Search Tool (BLAST) (Altschul et al., *J. Mol. Biol.* 215: 403-10(1990)) is available from several sources, including the National Center for Biological Information (NBCI, Bethesda, Md.) and on the Internet, for use in connection with the sequence analysis programs blastp, blasm, blastx, tblastn and tblastx. It can be accessed at http://www.ncbi.nlm.nih.gov/BLAST/. A description of how to determine sequence identity using this program is available at http://www.ncbi.nlm.nih.gov/BI-AST/blast help.html.

According to an embodiment, the present antibody comprises a heavy chain variable domain comprising the amino acid sequence of SEQ ID NO:25 or SEQ ID NO:29.

According to an embodiment, the present antibody additionally comprises a light chain variable domain comprising the following light chain CDR sequences: CDRL1 comprising SEQ ID NO:22, CDRL2 comprising SEQ ID NO:23 and CDRL3 comprising SEQ ID NO:24.

According to an embodiment, the present antibody comprises a light chain variable domain comprising the amino acid sequence of SEQ ID NO:26 or SEQ ID NO:30.

According to an embodiment, the present antibody comprises (i) a heavy chain variable domain of SEQ ID NO:25 and a light chain variable domain of SEQ ID NO:26; or (ii) a heavy chain variable domain of SEQ ID NO:29 and a light chain variable domain of SEQ ID NO:30.

The antibody of the present invention includes, but not limited to, monoclonal antibody, polyclonal antibody, human antibody, humanized antibody, chimeric antibody, single-chain Fvs (scFV), single-chain antibody, Fab fragment, F(ab') fragment, disulfide-linked Fvs (sdFV) and anti-idiotype (anti-Id) antibody, and epitope-binding fragment thereof.

The antibody of the this invention can be prepared in various forms of antibodies. For example, as shown in the Examples below, the present antibody can be prepared into not only Fab, but also whole antibody by the recombination of human constant regions with the heavy and light chain variable domains from the Fab.

According to an embodiment, the antibody of this invention is a monoclonal antibody. The term "monoclonal antibody" refers to an antibody molecule that has been obtained from a substantially identical antibody clone, which shows single-binding specificity and affinity for a specific epitope.

According to an embodiment, the antibody of this invention is produced from a hybridoma cell (Accession number: KCLRF-BP-00291).

According to an embodiment, the antibody of this invention comprises CDRs of an antibody produced from a hybridoma cell having an accession number of KCLRF-BP-00291. The hybridoma cell was deposited in the Korean Cell Line Bank under the Accession No. KCLRF-BP-00291 on Feb. 18, 2013.

According to an embodiment, the antibody of this invention is conjugated with functional molecules. The functional molecule includes chemical substances, radionuclides, cytotoxin, cytokines and chemokines, and detailed description thereto is provided below.

According to an embodiment, the antibody of this invention can treat cancers by decreasing/inhibiting/eliminating the activity of TM4SF5 proteins known as tumor-specific antigen.

II. Nucleic Acid Molecules and Recombinant Vectors

In another aspect of this invention, there is provided a nucleic acid molecule encoding a heavy chain variable domain of the anti-TM4SF5 antibody or its antigen-binding fragment.

In still another aspect of this invention, there is provided a nucleic acid molecule encoding a light chain variable domain of the anti-TM4SF5 antibody or its antigen-binding fragment.

The term used herein "nucleic acid molecule" comprehensively refers to a DNA (gDNA and cDNA) or RNA molecule, and the basic nucleotides of nucleic acid molecule also include analogues with modified sugar or base as well as natural nucleotides (Scheit, Nucleotide Analogs, John Wiley, New York (1980); Uhlman and Peyman, Chemical Reviews, 90:543-584 (1990)). The sequence of the present nucleic acid molecule encoding the variable region of heavy and light chain could be modified. Such modification includes addition, deletion and non-conservative or conservative substitution of nucleotides.

According to an embodiment, the nucleic acid molecule encoding a heavy chain variable domain comprises the nucleotide sequence of SEQ ID NO:27 or SEQ ID NO:31, and the nucleic acid molecule encoding a light chain variable domain comprises the nucleotide sequence of SEQ ID NO:28 or SEQ ID NO:32.

The nucleic acid molecule of this invention also includes a nucleotide sequence sharing substantial homology with the above nucleotide sequence. The substantial homology means the nucleotide sequence sharing homology of at least 80%, more preferably 90% and most preferable 95% by sequence alignment analysis using maximal alignment between the nucleotide sequence of this invention and other random sequences and algorithm ordinarily known to those skilled in the art.

In still further aspect of this invention, there is provided a recombinant vector comprising (a) the present nucleic acid molecule encoding a heavy chain variable domain; and/or (b) the present nucleic acid molecule encoding a light chain variable domain.

The term used herein "vector" is a tool for expressing a target gene in a host cell, including a plasmid vector; a cosmid vector; and a virus vector such as a bacteriophage vector, an adenovirus vector, a retrovirus vector and an adeno-associated virus vector, and preferably a plasmid vector.

According to an embodiment, the nucleic acid molecules encoding the variable region of light and heavy chain are operatively linked to a promoter.

The term used herein "operatively linked" refers to functional linkage between a nucleic acid expression control sequence (e.g., a promoter, signal sequence, or array of transcription factor binding sites) and a second nucleic acid sequence, wherein the expression control sequence affects transcription and/or translation of the nucleic acid corresponding to the second sequence.

According to an embodiment, the recombinant vector comprises (i) a nucleic acid molecule encoding a heavy chain variable domain of SEQ ID NO:27 and a nucleic acid molecule encoding a light chain variable domain of SEQ ID NO:28; or (ii) a nucleic acid molecule encoding a heavy chain variable domain of SEQ ID NO:31 and a nucleic acid molecule encoding a light chain variable domain of SEQ ID NO:32.

The vector system of this invention may be performed by various methods known to those skilled in the art and its practical method is described in Sambrook et al., *Molecular Cloning, A Laboratory Manual*, Cold Spring Harbor Laboratory Press (2001), which is herein incorporated by reference.

Typically, the vector of this invention may be constructed as cloning or expression vector. In addition, the vector of this invention may be constructed using a prokaryotic or eukaryotic cell as a host cell. For instance, it is common to include a strong promoter for transcription (e.g., tac promoter, lac promoter, lacUV5 promoter, lpp promoter, $p_L^\lambda$ promoter, $p_R^\lambda$ promoter, rac5 promoter, amp promoter, recA promoter, SP6 promoter, trp promoter and T7 promoter, and so on), a ribosomal binding site for translation initiation, and a transcription/translation termination sequence where each a vector of this invention and a prokaryotic cell is used in an expression vector and the host cell, *E. coli* (e.g., HB101, BL21, DH5α, etc.) as a host cell may utilize a promoter and operator region for tryptophan biosynthesis pathway (Yanofsky, C, *J. Bacteriol.*, 158:1018-1024 (1984)), and $p_L^\lambda$ promoter (Herskowitz, I. and Hagen, D., *Ann. Rev. Genet*, 14:399-445 (1980)) as a regulatory region. *Bacillus* as the host cell may use the promoter of a toxic protein gene of *Bacillus thuringiensis* (*Appl. Environ. Microbiol.* 64:3932-3938(1998); *Mol. Gen. Genet.* 250:734-741(1996)), or any promoter enabling to be expressed in *Bacillus* as the regulatory region.

The suitable vector used in this invention might be constructed by manipulating a plasmid (example: pCL, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19), a phage (example: λgt4·λB, λ-Charon, λΔzl and M13) or a virus (example: SV40) commonly used by one ordinarily skilled in the art.

According to an embodiment, the recombinant vector is one having a cleavage map of FIG. 17.

On the other hand, where the present vector is an expression vector, and its host cell is an eukaryotic cell, the promoter derived from genome of animal cell (example: methallothionein promoter, β-actin promoter, human hemoglobin promoter and human muscle creatine promoter) or mammalian virus (example: adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of moloney virus, Epstein barr virus (EBV) and Rous sarcoma virus (RSV)) might be used, and polyadenylated sequence might be commonly used as the transcription termination sequence. In an embodiment, the vector of this invention includes CMV promoter.

The vector of this invention could be fused with other sequences to purify an antibody expressed from it. For example, a fused sequence includes glutathione-S-transferase (Pharmacia, USA); maltose-binding protein (NEB, USA); FLAG (IBI, USA); 6× His (hexahistidine; Quiagen, USA); a tag sequence such as Pre-S1 and c-Myc; a leader sequence such as OmpA and PeIB; and so on. Since the protein expressed in the vector of the present invention is antibody, expressed antibody could be also purified throughout protein A column in an easy manner without additive sequences for purification.

On the other hand, the expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

In the vector expressing the antibody or its part of the present invention, it is possible to utilize one vector system co-expressing the light and heavy chain in single vector or the other vector system expressing each light and heavy chain in independent vector. In latter system, both vectors are introduced into the host cell by co-transformation or targeted transformation. Co-tansformation is a method in which each vector DNA encoding a light and heavy chain gene is simultaneously introduced into the host cells and then the vectors expressing both light and heavy chains are selected. In targeted transformation, cells transformed with a vector containing a light chain (or heavy chain) gene are selected, and the selected cells expressing the light chain (or heavy chain) are again transformed with a vector containing a heavy chain (or light chain) gene to finally select cells expressing both light and heavy chains. As described in the examples below, the antibody was prepared by the vector system co-expressing the light and heavy chains in a single vector. In the Examples, antibodies were prepared using a vector system co-expressing the light ($V_L$ and $C_L$) and heavy chain ($V_H$ and $C_{H1}$) in single vector.

III. Transformants

In still another aspect of this invention, there is provided a host cell comprising the above-described recombinant vector. The host cell may be transformed with the recombinant vector.

The host cells in which the present vector is stably and successively cloned and expressed, also utilize any one known to those skilled in the art, for example prokaryotic host cells including *Escherichia coli, Bacillus* sp. strains such as *Bacillus subtilis* and *Bacillus thuringiensis, Streptomyces, Pseudomonas* (e.g., *Pseudomonas putida, Proteus mirabilis*) or *Staphylococcus* (e.g., *Staphylocus carnosus*), but not limited to.

The suitable eukaryotic host cell of the above vector includes fungi (e.g., *Aspergillus* species), yeasts (e.g., *Pichia pastoris, Saccharomyces cerevisiae, Schizosaccharomyces* and *Neurospora crassa*), other lower eukaryotic cells and cell derived from higher eukaryotic cells such as insect cells. In addition, plant- or mammalian-derived cells might be used as the host cells.

In this specification, "transformation" and/or "transfection" introduced into the host cells also includes any one of methods by which the nucleic acid is introduced into organisms, cells, tissues or organs and may be performed by selecting a suitable standard technique according to the host cells, as known to those skilled in the art. These standard techniques include, but not limited to, electroporation, protoplast fusion, $CaPO_4$ precipitation, $CaCl_2$ precipitation, agitation with silicon carbide fiber, Agrobacteira-mediated transformation, and PEG-, dextran sulfate-, lipopectamine- and dry/inhibition-mediated transformation.

IV. Method of Preparing Anti-TM4SF5 Antibodies or Antigen-Binding Fragment Thereof In still further aspect of this invention, there is provided a method of preparing the anti-TM4SF5 antibodies or antigen-binding fragment thereof, comprising: (a) culturing the host cell of the present invention; and (b) expressing an anti-TM4SF5 antibodies or antigen-binding fragment thereof in the host cell.

The culture of transformed host cells in the antibody preparation may be carried out according to suitable media and culture conditions well-known in the art. The culture process may be feasible manipulated according to selected strains known to those skilled in the art. Various culture processes are disclosed in various references (for example, James M. Lee, *Biochemical Engineering*, Prentice-Hall International Editions, 138-176). Cell culture is divided into suspension and adhesion culture method according to cell growth pattern and into batch, fermentation and continuous culture according to culture method. The medium used in the culture has to satisfy required conditions of particular strain.

The medium for animal cell culture includes various carbon sources, nitrogen sources and trace elements. The example of carbon sources to be used includes a carbohydrate such as glucose, sucrose, lactose, fructose, maltose, starch and cellulose, a lipid such as soybean, sunflower, castor and coconut oil, a fatty acid such as palmitic acid, stearic acid and linoleic acid, an alcohol such as glycerol and ethanol, and an organic acid such as acetate. These carbon sources may be used either alone or in combination with each other. The example of nitrogen sources to be used includes an organic nitrogen source such as peptone, yeast extract, malt extract, corn steep liquid (CSL) and soybean-wheat, and an inorganic nitrogen source such as urea, ammonium sulfate, ammonium chloride, ammonium phosphate, ammonium carbonate and ammonium nitrate. These nitrogen sources may be used either alone or in combination with each other. The medium may include not only $KH_2PO_4$, $K_2HPO_4$ and sodium-containing salts thereof as a phosphate source but also metal salt such as magnesium sulfate and iron sulfate. In addition, the medium may include amino acids, Vitamins and suitable precursors.

During culture, pH of culture solution may be adjusted by adding chemical compounds such as ammonium hydrate, potassium hydrate, ammonia, phosphate and sulfate in a predetermined manner. Bubble production may be also inhibited using an antifoaming agent such as polyglycol ester during culture. Meanwhile, oxygen or oxygen-containing gas (e.g., air) is introduced into culture to maintain aerobic state of culture. The temperature of culture is maintained at a range of from 20° C. to 45° C., and preferably from 25° C. to 40° C.

Antibodies obtained by culturing of transformed host cells may be used in unpurified condition and may be used through purification with high-purity according to further various conventional methods, for example dialysis, salt precipitation and chromatography. Among them, chromatography is used as the most useful method and kinds and orders of column may be selected from ion-exchange chromatography, size-exclusion chromatography and affinity chromatography according to characteristics of antibody, culture methods, and so on.

V. The Prevention or Treatment of Cancers

In still further aspect of this invention, there is provided a pharmaceutical composition for preventing or treating a cancer, comprising: (a) a pharmaceutically effective amount of the anti-TM4SF5 antibody or antigen-binding fragment thereof; and (b) a pharmaceutically acceptable carrier.

In still further aspect of this invention, there is provided a method of preventing or treating a cancer in a subject in need thereof, comprising administering to the subject a pharmaceutically effective amount of the pharmaceutical composition.

The present antibodies can be used to prevent and treat cancers together with general pharmaceutically acceptable carriers, since they inhibit the growth, invasion and metastasis of cancers expressing TM4SF5 by binding to TM4SF5 with a high affinity.

The term used herein "prevention" is used in the broadest sense to include, complete or partial blocking and slowing down of the progression of the disease as well as the delay of the unset of the more serious form of the disease, and the term "treatment" includes partial or total inhibition of cancer growth, as well as partial or total destruction of the cancer cells.

According to an embodiment, the cancer is one expressing TM4SF5, for example, liver cancer, colorectal cancer, pancreatic cancer, lung cancer, gastric cancer, rectal cancer, soft-tissue sarcoma, colon cancer, carcinoma of the papilla vateri, nonendocrine lung tumor, bronchial carcinoid tumor and so on.

The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered via the oral or parenterally. When the pharmaceutical composition of the present invention is administered parenterally, it can be done by intravenous, subcutaneous, intramuscular, intraperitoneal, endothelial, local, spleen, lung or rectal administration. For oral administration, active ingredients of oral compositions can be coated or formulated to be protected from hydrolysis in stomach. In addition, the pharmaceutical compositions can be administered by random device in which active ingredients are moved into targeted cells.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.0001-100 mg/kg (body weight). The term "pharmaceutically effective amount" refers to an amount suitable to prevent or treat the cancer.

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The antibody compositions of this invention may be independently administered as a therapeutic agent or be sequentially or simultaneously administered with a conventional therapeutic agent.

The antibody of this invention may be administered to a subject in the form of a conjugate of antibody-functional molecule to treat cancers. The functional molecule includes chemical substances, radionuclides, immunotherapeutic agents, cytokines, chemokines, toxins, biological agents and enzyme inhibitors. Preferably, the functional molecule is chemical substances, radionuclides, cytokines or chemokines. The chemical substance is an antitumor agent such as, but not limited to, acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol, beta-2'-deoxythioguanosine, bisantrene HCI, bleomycin sulfate, busulfan, buthionine sulfoximine, BWA 773U82, BW 502U83/HCI, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCI, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol™., flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCI, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome-encapsulated doxorubicin, lomustine, Ionidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, cytosine arabinoside, etoposide, melphalan, taxotere, taxol and mixtures thereof.

VI. Methods of Detecting TM4SF5 Proteins and Diagnosis of Cancers

In still further aspect of this invention, there is provided a method for identifying (detecting) the presence of TM4SF5 protein in a sample, using the present antibody or antigen binding fragment thereof.

In still another aspect of this invention, there is provided a kit for detecting TM4SF5 protein comprising the present antibody or antigen binding fragment thereof.

The antibody of this invention can detect TM4SF5 protein in biological samples. The term "biological sample" used herein is meant to broadly encompass a tissue, a cell, whole blood, serum, plasma, oral fluid, urine, lymph, cerebrospinal fluid, autoptical sample of tissue (e.g., brain, skin, lymph node and spinal cord), supernatant of cell culture, eukaryotic cell lysate, and bacteria expression system.

According to an embodiment, the cell as a biological sample is cancer cells.

According to an embodiment, the kit of this invention is for diagnosing a cancer. The present kit can be used to identify the development of cancers by reacting manipulated or non-manipulated biological sample with the antibody of the present invention.

The detection of TM4SF5 in biological samples may be performed by detecting an antigen-antibody complex using colormetric method, electrochemical method, fluorimetric method, luminometry, particle counting method, visual assessment or scintillation counting method. The detection is for the detection of antigen-antibody complex, and is carried out using various labels. Specific examples of the labels encompass enzymes, fluorescent substances, ligands, luminescent substances, microparticles, and radioactive isotopes.

Suitable examples of materials to be used as a label include acetylcholine esterase, alkaline phosphatase, β-D-galactosidase, horseradish peroxidase and β-lactamase as an enzyme; fluorescein, $Eu^{3+}$, $Eu^{3+}$ chelate and cryptate as a fluorescent; biotin-derivatives as a ligand; acridinium ester, isoluminol derivatives as a luminescent; colloidal gold, colored latex as a microparticle; and $^{57}Co$, $^{3}H$, $^{125}I$, $^{125}I$-Bonton Hunter reagent as a radioactive isotopes.

According to an embodiment, the antigen-antibody complex may be detected by using Enzyme-linked immunosorbent assay (ELISA). ELISA techniques include a direct ELISA using a labeled antibody which recognizes an antigen adhered to a support body; an indirect ELISA using a labeled secondary antibody which recognizes a captured antibody of an antigen-antibody complex wherein the antigen adhered to a support body; a direct sandwich ELISA using another labeled antibody which recognizes an antigen of an antigen-antibody complex adhered to a support body; and an indirect sandwich ELISA using another labeled secondary antibody which recognizes an antibody, after reacting with the antibody which recognizes an antigen of an antigen-antibody complex adhered to a support body. The present antibody may have a detectable label, otherwise the antigen-antibody complex may be detected by treating another antibody which can capture the monoclonal antibody and has a detectable label.

The features and advantages of this invention will be summarized as follows:

(i) The present invention provides an antibody or antigen binding fragment thereof, that binds to TM4SF5, and uses thereof.

(ii) The antibody of this invention inhibits the growth, metastasis and invasion of cancer cells expressing TM4SF5 by binding to a tumor-specific antigen, TM4SF5, with high affinity, and therefore can be used to diagnose, prevent or treat various cancers expressing TM4SF5.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Production of the Mouse Anti-TM4SF5 Monoclonal Antibody (2D4-18)

Female BALB/c mice were injected i.p. with hTM4SF5 peptide ($^{138}$NRTLWDRCEAPPRV$^{151}$) on four occasions at 10 day intervals. Splenocytes were harvested from immunized spleens and fused with HAT-sensitive SP2/0 mouse myeloma cells in the presence of 40% (w/v) polyethylene glycol in accordance with the standard hybridoma technique (Yokoyama W M, et al. *Curr Protoc Immunol* Chapter 2, Unit 2.5(2006)). Culture supernatants of hybridoma cells were tested for binding to hTM4SF5 peptide by ELISA, and positive hybridoma cells were then screened. ELISA-positive hybridoma cell populations were subcloned and then injected into i.p. cavity to generate ascites in BALB/c mice. The anti-TM4SF5 monoclonal antibody (2D4-18) was purified from the ascites fluid by protein A column chromatography (Amersham Pharmacia Biotech).

ELISA

Mouse sera were obtained by orbital bleeding before each injection as well as by sacrifice 10 days after final injection. To determine the amounts and titers of total IgG, 96-well immunoplates (Nalgen Nunc International) were coated with 5 μg/ml of hTM4SF5 peptide and then blocked for 2 hr with 0.05% of Tween-20 in PBS (PBST) containing 1% BSA. After the blocking solution was removed, 100•μl of culture supernatant was added, incubated for 2 hr at room temperature, washed with PBST, and then incubated with detecting antibody such as anti-IgG antibody conjugated with horseradish peroxidase for 2 hr. A colorimetric assay was developed with a TMB substrate solution, and the absorbance at 450 nm was measured using a Spectra Max 250 microplate reader.

Surface Plasmon Resonance (SPR) Analysis

Affinity of anti-hTM4SF5 monoclonal antibody binding to human TM4SF5 peptide (hTM4SF5) and mouse TM4SF5 peptide (mTM4SF5) was measured using Biacore T100 (Biacore) at 25° C. Biotinylated peptides were captured on individual flow cell surface of a CM4 sensor chip coated with streptoavidin. Biotin served as a negative control. Anti-TM4SF5 monoclonal antibody at concentrations ranging from 2 to 32 nM was injected at a flow rate of 30 ml/min. Data were evaluated using Biacore Bia evaluation software (version 3.0).

Tissue Microarrays and Immunohistochemistry

The following arrays were used: Liver cancer tissues (A204 and A204(II)), colon cancer tissues (A203(VII)) and colon cancer tissues-liver metastasis (A203 III). Liver cancer tissue arrays consisted of duplicate HCC tissue cores of varying histotypes and four or eight non-neoplastic corresponding samples on each slide. Colon cancer tissue array (A203(VII)) contained 45 cases consisted of duplicate colon cancer tissue cores of varying histotypes and eight non-neoplastic corresponding samples on each slide. Colon cancer tissues-liver metastasis (18 cases) with corresponding colon normal tissues consisted of four spots from each cancer case and 18 non-neoplastic corresponding samples on each slide. Slides were deparaffinized in xylene, rehydrated, and treated with fresh 0.3% hydrogen peroxide in methanol for 15 min. Tissue arrays were stained according to the standard procedure with anti-TM4SF5 monoclonal antibody.

Cell Culture

The human HCC cell lines such as Huh-7, Hep3B and SNU-761, and human colon cancer cell lines HT-29 and LoVo, and mouse colon cancer cell line CT-26 were obtained from the Korean Cell Line Bank (Seoul, Korea). The mouse hepatoma cell line BNL-HCC was obtained from ATCC. Hep3B, BNL-HCC and CT-26 cells were maintained in DMEM medium containing 10% fetal bovine serum (FBS; Hyclone), 2 mM glutamine, 100 U/ml penicillin and 100 μg/ml streptomycin. The other cell lines were maintained in an RPMI 1640 medium with 10% FBS, 25 mM HEPES, 100 U/ml penicillin and 100 μg/ml streptomycin. All cells were cultured at 37° C. in an atmosphere of 95% air and 5% $CO_2$.

Detection of TM4SF5 mRNA Expression

To analyze the TM4SF5 expression, we performed RT-PCR and FACS analysis. Total RNAs were extracted with an RNeasy Mini Kit (Qiagen), and the cDNA was generated. The standard PCR reaction was performed for 25 cycles with the following primer sets: mouse GAPDH (SEQ ID NOs:1 and 2, 501 bp); mouse TM4SF5 (SEQ ID NOs:3 and 4, 174 bp), human β-actin (SEQ ID NOs:5 and 6, 500 bp); human TM4SF5 (SEQ ID NOs:7 and 8, 408 bp).

MTT Assay

The growth of cancer cells treated with anti-TM4SF5 monoclonal antibody (10 μg/ml) for 5 days was determined by MTT assay using a 3-(4,5-dimethylthiazole-2-yl)-2,5-diphenyl tetrazolium bromide (MTT, Sigma-Aldrich) solution. The MTT solution was added to each well at the indicated time periods and the plates were incubated for an additional 4 hr at 37° C. After the removal of the medium, the formazan crystals were solubilized in DMSO. The color development was monitored by means of a spectrophotometer at 595 nm with a reference wavelength of 650 nm.

Cell Migration and Invasion Assay

Trans-well chambers (Corning Costar) with 8 μm porosity were used in the assay. For migration assay, the lower sides of trans-well chamber membranes were coated with 10 μg/ml of gelatin. For invasion assay, the upper sides and lower sides of the chamber membranes were coated with 1.2 mg/ml of Matrigel (BD Biosciences) and 10 μg/ml of gelatin, respectively. Cells (Huh-7 or CT-26) were suspended ($5 \times 10^4$ cells/ml) in a serum-free media with normal IgG or anti-TM4SF5 monoclonal antibody, and placed on the top of the trans-well. RPMI medium containing 5% FBS was placed in the lower chamber. After incubation for 12 hr, the invaded cells on the lower surfaces of the filters were fixed with 4% paraformaldehyde for 30 min, stained with 0.005% crystal violet for 30 min, and counted under a microscope.

Wound-Healing Assay

For wound-healing assays, $1 \times 10^6$ cells (Huh-7 or CT-26) were placed in a 6-well plate, cultured overnight to confluence in a serum-containing media, and the monolayer was wounded with a pipette tip. Normal IgG or the anti-hTM4SF5 monoclonal antibody (10 µg/ml) were applied for the indicated periods. The cells were fixed with 4% paraformaldehyde for 30 min and stained with Giemsa for 30 min.

Animals

Four-week-old male BALB/cAnNCri-nu/nu mice and BALB/c mice were obtained from Central Lab. Animal, Inc., and the mice were maintained under specific-pathogen-free condition. All procedures involving animal studies are in accordance with the recommendations in the Guide for the Care and Use of Laboratory Animals of the National Veterinary Research & Quarantine Service of Korea. The mice were sacrificed under Zoletil 50+Rompun anesthesia, and all efforts were made to minimize suffering.

Hepatocellular Carcinoma Mouse Model

30 BALB/cAnNCri-nu/nu mice and 30 BALB/c mice were inoculated subcutaneously in the dorsal right flank with $5 \times 10^6$ Huh-7 cells containing 50% Matrigel (BD biosciences) and $5 \times 10^6$ BNL-HCC cells containing 50% Matrigel, respectively. When tumors reached 5 mm in diameter, mice were randomly divided into three treatment groups (eight mice/each group) such as PBS, IgG control, and anti-TM4SF5 monoclonal antibody. The antibodies (25 mg/kg) were injected twice weekly in the intraperitoneal cavity. The tumor diameters were measured 4 days (or 7 days) interval with calipers for six weeks after the injection of cancer cells, and tumor volumes were calculated using the formula width$^2 \times$length/2. BALB/cAnNCri-nu/nu mice were sacrificed when the tumor size reached a volume $\pm 2000$ mm$^3$, and the weight of tumors was assessed. BALB/c mice were sacrificed 10 weeks after the tumor cell implantation, and the weight of tumors were assessed.

Biodistribution Imaging In Vivo

Anti-TM4SF5 monoclonal antibody and normal mouse IgG was conjugated with DyLight 750-fluorescence (Thermo Scientific) and purified according to the manufacturer's specifications. 50 µg of DyLight 750-fluorescence-labeled anti-TM4SF5 monoclonal antibody or DyLight 750-fluorescence-labeled normal mouse IgG were injected into intraperitoneal cavity of BALB/c mice. The distribution profiles of anti-TM4SF5 monoclonal antibody were quantified by in vivo fluorescence using the real-time IVIS imaging system 200 (Xenogen Corp.) at the indicated time intervals. The data were analyzed with the aid of Living Image 2.50 software (Xenogen Corp.). To determine the distribution of DyLight 750-fluorescence-labeled anti-TM4SF5 monoclonal antibody in the HCC tumor tissues, the tissues were removed aseptically at 72 hr post intraperitoneal cavity injection. The tissues were frozen and cut into 4 µm thick slices. The slices were stained with SYTOX Green dye (Invitrogen), and the mounted samples were scanned with an LSM 510 META NLO.

Colon Cancer Mouse Model

30 BALB/cAnNCri-nu/nu mice and 30 BALB/c mice were inoculated subcutaneously in the dorsal right flank with $5 \times 10^6$ HT-29 cells containing 50% Matrigel (BD biosciences) and $5 \times 10^6$ CT-26 cells containing 50% Matrigel, respectively. When tumors reached 5 mm in diameter, mice were randomly divided into three treatment groups (eight mice/each group) such as PBS, IgG control, and anti-TM4SF5 monoclonal antibody 2D4-18. The antibodies (25 mg/kg) were injected twice weekly in the intraperitoneal cavity. The tumor diameters were measured 5 days (or 2 days) interval with calipers for 30 days after the injection of cancer cells, and tumor volumes were calculated using the formula width$^2 \times$length/2. BALB/cAnNCri-nu/nu mice were sacrificed when the tumor size reached a volume $\pm 2000$ mm$^3$, and the weight of tumors was assessed. BALB/c mice were sacrificed 18 days after the tumor cell implantation, and the weight of tumors were assessed.

Lung Metastasis

For the metastatic cancer animal experiment, BALB/c mice were injected intravenously (via tail veins) with $2 \times 10^5$ mouse CT-26 colon cancer cells (PBS control n=8, colon cancer cells n=36). On day 5, cancer cell injected mice were randomly divided into three treatment groups such as PBS, IgG control, and anti-TM4SF5 monoclonal antibody (n=12 per each group). The antibodies (25 mg/kg) were injected twice weekly in the tail veins. On day 20, mice were sacrificed and the lung was weighed.

Histology

For a histopathological examination, the tumors and organs were removed and fixed in a 4% buffered formalin solution overnight, embedded in paraffin, and cut into 5 µm thick sections. The deparaffinized sections were then stained with hematoxylin and eosin (H&E).

Immunohistochemistry

To identify the expression of TM4SF5, the specimens were stained with anti-TM4SF5 monoclonal antibody using standard procedures. The specimens were cut into 5 µm thick sections. After deparaffinization by xylene and rehydration in ethanol, endogenous peroxidase activity was blocked with 0.3% hydrogen peroxide and 10% methanol in PBS, followed by preincubation in PBS containing 0.2% Triton X-100 (PBST) and 3% bovine serum albumin for 2 hr. The sections were then incubated overnight in PBST containing anti-TM4SF5 monoclonal antibody (1:400) at 4° C., followed by incubation with biotinylated secondary antibody. They were reacted with streptavidin-biotin peroxidase, then reacted with 3',3'-diaminobenzinidine (0.5 mg/ml) and hydrogen peroxide, and counterstained with H&E. After rinsing, the sections were mounted, dehydrated, and covered with cover slips. All images were examined using a Nikon Eclipse E-200 microscope (Nikon, Tokyo, Japan).

Cloning of the Variable Heavy and Light Domains of Anti-TM4SF5 Monoclonal Antibody 2D4-18

Hybridoma cells (2D4-18) producing anti-TM4SF5 monoclonal antibody 2D4-18 were cultured and isotyped using a mouse monoclonal antibody isotyping kit (Dipstick format, Bibco BRL or Roche, Mannheim, Germany). Total RNAs were extracted from hybridoma cells with an RNeasy Mini Kit (Qiagen), and the cDNAs were generated. To clone the sequences for the variable heavy and light domains ($V_H$ and $V_L$) of anti-TM4SF5 monoclonal antibody 2D4-18, the resultant cDNAs were amplified using Vent polymerase (NEB) with the following primer sets. For heavy chain primers, IGG2A (SEQ ID NO:9) and 5'MH2 (SEQ ID NO:10) were used. For kappa chain primers, 3'Kc (SEQ ID NO:11) and 5'Mk (SEQ ID NO:12) were used. The standard PCR reaction was performed for 25 cycles. The PCR products were directly ligated into the pGEM-T easy vector (Promega). Cloned mouse Ig inserts were analyzed by DNA sequencing.

Expression of the Antigen Binding Fragment (Fab) of Anti-TM4SF5 Monoclonal Antibody 2D4-18

Sequences encoding the variable heavy and light domains of anti-TM4SF5 monoclonal antibody 2D4-18 ($V_H$ and $V_L$) were amplified and sequentially subcloned into bacterial expression vector FabE using Sfi I and BstX I, respectively peon et al. *Mol. Immunol.* 44: 827-836(2007); Kwon et al. *Oncol. Rep.* 18: 513-517(2007)). The primer sequences used in this study are as followings: For $V_H$ (391 bp, SEQ ID NOs:13 and 14; 368 bp, SEQ ID NOs:15 and 14), For $V_L$ (399 bp, SEQ ID NOs:16 and 17; 381 bp, SEQ ID NOs:18 and 17. The recombinant expression plasmids named as pFabE-2D4-18 or pFabE-2D4-18(1) were verified by restriction analysis and DNA sequencing. pFabE-2D4-18 or pFabE-2D4-18(1) was transformed into TG1 *E. coli* cells, and expression of recombinant protein was optimized and verified at a small scale by western blotting using anti-PreS1 antibody and anti-His antibody. For large scale production and purification of recombinant Fab (pFabE-2D4-18 and pFabE-2D4-18(1)), 500 ml culture was treated with 0.5 mM IPTG and incubated at 18° C. for 16 hr. The culture supernatant was harvested by centrifugation and poured onto Ni-NTA affinity column (Clontech) to isolate properly folded and assembled Fab proteins with the aid of His tag in the $V_H$-$C_H$ fusion protein. Column bound recombinant Fab was eluted by 10 mM imidazole (pH 8.0), and the protein solution was dialyzed and concentrated using centricon by centrifugation (3,500×g) at 4° C.

Functional Effect of Recombinant Fab of Anti-TM4SF5 Monoclonal Antibody 2D4-18 on Hepatocellular Carcinoma Cells To measure the growth of cells, MTT assay was performed as described above. The growth of cancer cells (Hep3B and Huh-7) treated with recombinant Fab of monoclonal antibody 2D4-18 (10 μg/ml) for 5 days was determined by MTT assay.

Binding Affinity of Recombinant Fab of Anti-TM4SF5 Monoclonal Antibody

Affinity of recombinant Fab of anti-TM4SF5 monoclonal antibody 2D4-18 to hTM4SF5 was measured using Biacore T100 (Biacore) at 25° C. Biotinylated peptides were captured on individual flow cell surface of a CM4 sensor chip coated with streptoavidin. Biotin served as a negative control. Recombinant Fab of anti-TM4SF5 monoclonal antibody at concentrations ranging from 100 to 1,600 nM was injected at a flow rate of 30 ml/min. Data were evaluated using Biacore Bia evaluation software (version 3.0).

Results

Production of Anti-TM4SF5 Monoclonal Antibody 2D4-18

Figure 1A:
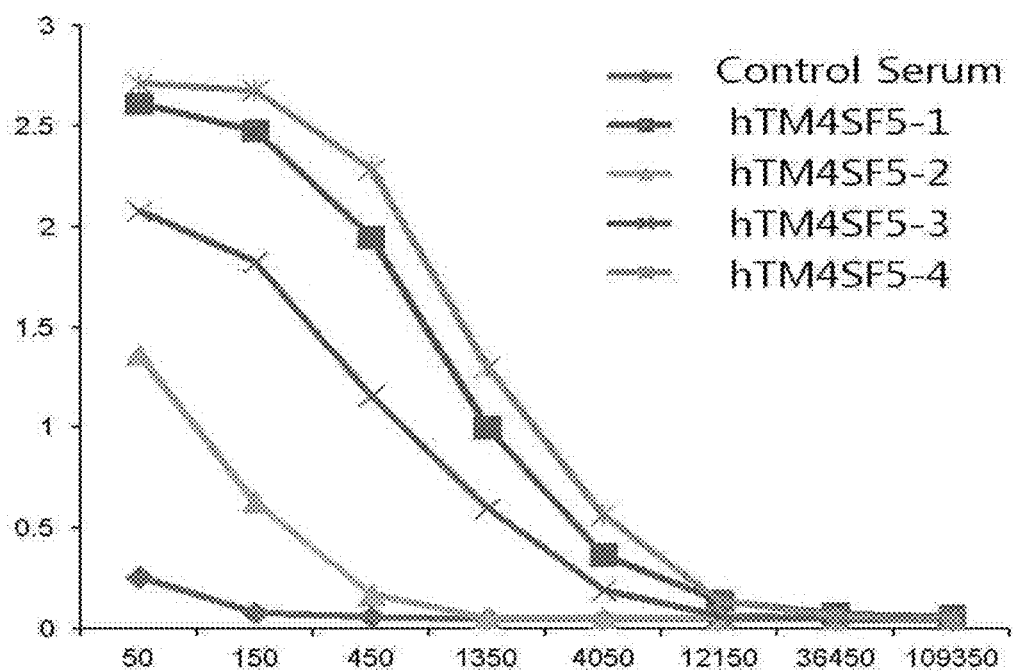
FIG. 1A-E represents screening of hybridoma clone producing anti-TM4SF5 monoclonal antibody.
Figure 1B:
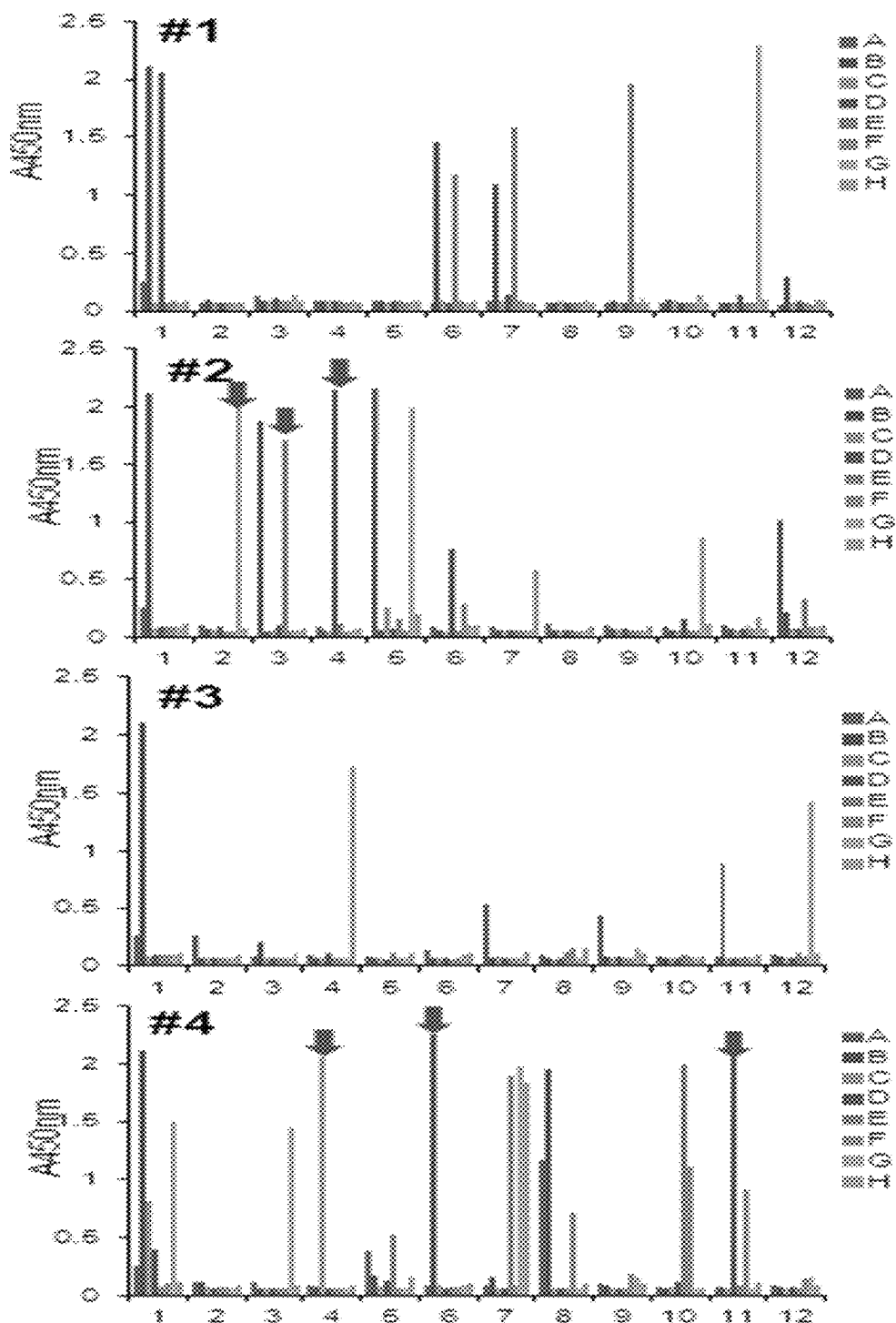
Figure 1C:
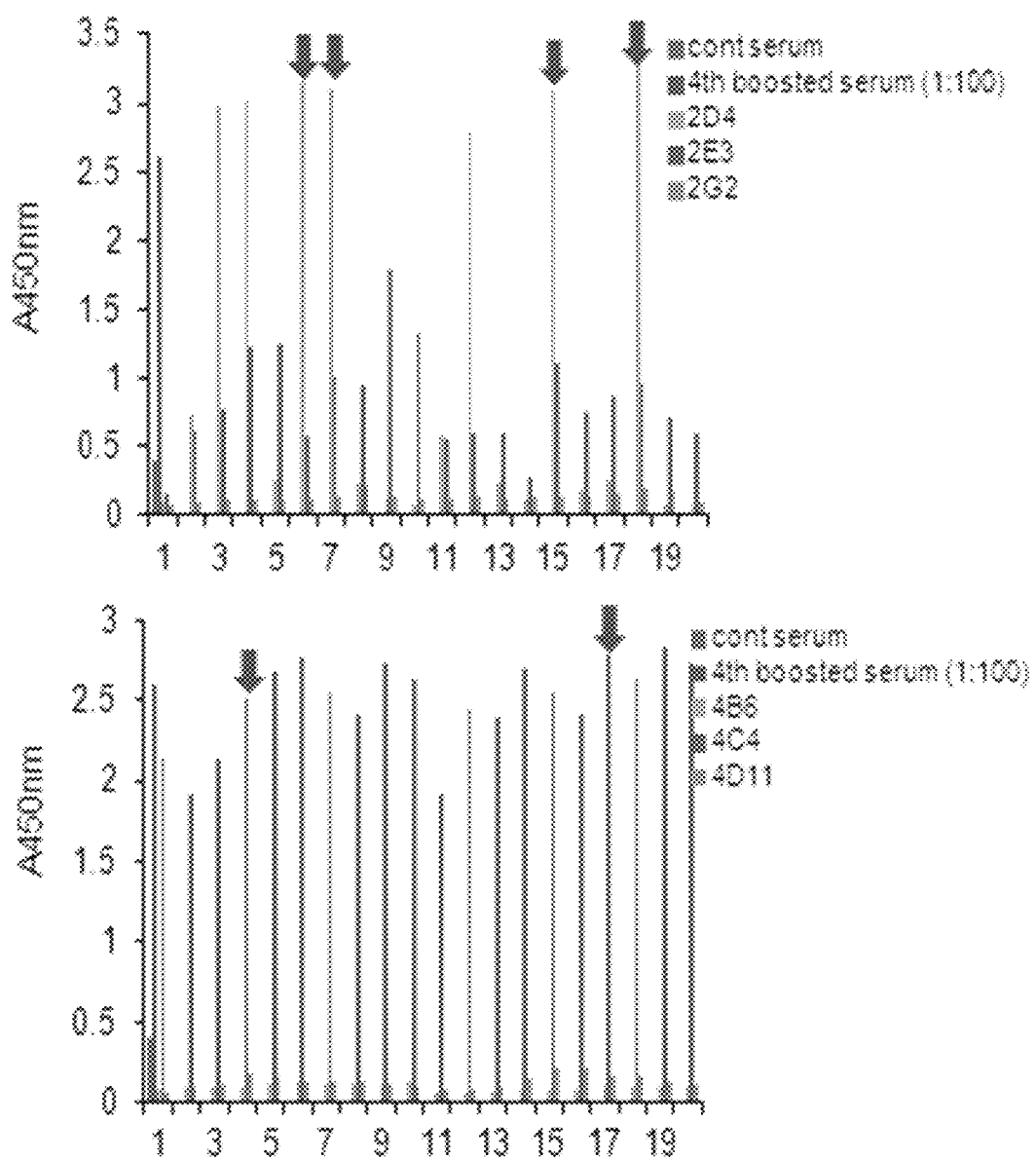
Figure 1D:
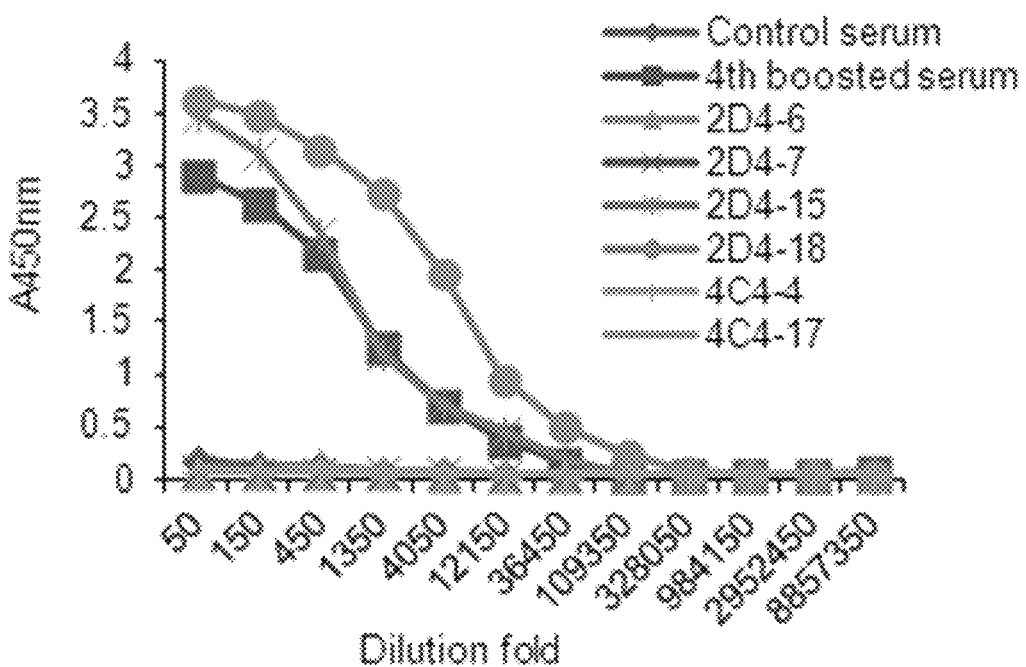
Figure 1E:
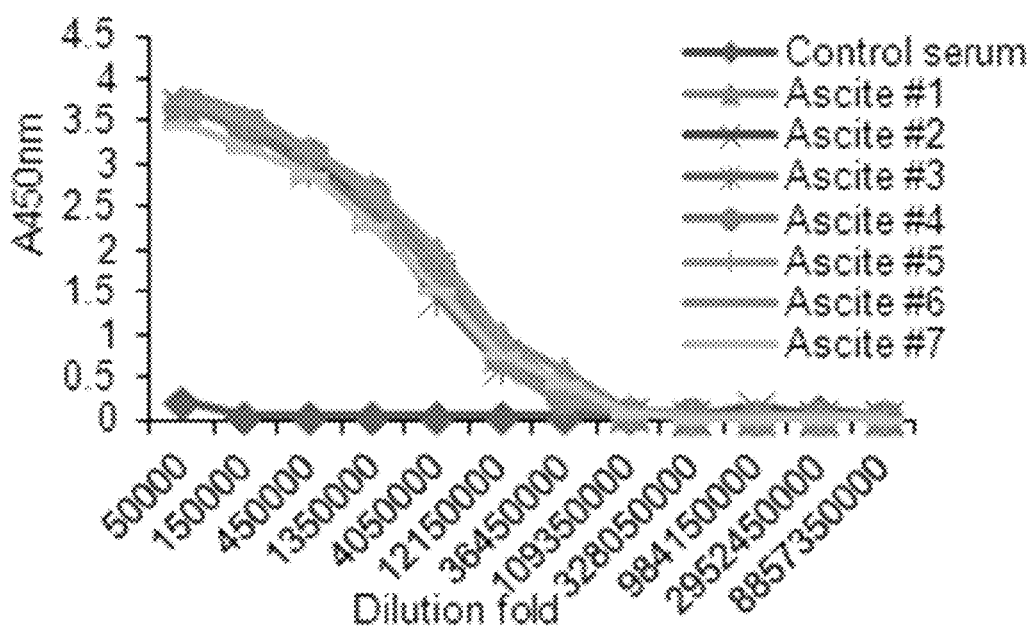

Following four times immunization, the titration curves of antibody against the hTM4SF5 peptide in mice sera were obtained by ELISA (FIG. 1a). Three days after the last booster, spleen of the mouse with the highest antibody titer (hTM4SF5-4) was obtained and the spleen cells were fused with SP2/0 myeloma cells by conventional hybridoma technology. After 14 days, supernatants were analyzed by an ELISA method to screen hybridoma cells secreting specific antibodies against hTM4SF5 peptide. Through the screening procedure, we isolated six hybridoma cells (2D4, 2E3, 2G2, 4B6, 4C4 and 4D11) reactive to hTM4SF5 peptide (FIG. 1b). The six hybridoma cells were further analyzed for the production of monoclonal antibody after subcloning procedure by limiting dilution method (FIG. 1c). Six hybridoma clones (four 2D4 derivatives and two 4C4 derivatives) were selected and injected into i.p. cavity to generate ascites in BALB/c mice. The ascites were screened by ELISA to detect hybridomas highly secreting specific antibodies against hTM4SF5 peptide. Finally, one hybridoma clone was selected for the production of monoclonal antibody (2D4-18) (FIG. 1d). The hybridoma cell was deposited in the Korean Cell Line Bank under the Accession No. KCLRF-BP-00291 on Feb. 18, 2013. When the clone was injected into i.p. cavity of 7 BALB/c mice, all the ascites produced anti-hTM4SF5 peptide-specific antibody (FIG. 1e). The anti-TM4SF5 monoclonal antibody 2D4-18 was purified from the ascites fluid by protein A column chromatography and the purity was measured over 99% (FIG. 2). The isotype of the antibody was IgG2a.

Affinity of Anti-TM4SF5 Monoclonal Antibody 2D4-18

We quantitatively measured binding affinity of TM4SF5-targeted mAb (2D4-18) using a surface plasmon resonance biosensor, Biacore. As a result, the mAb reacts with human TM4SF5 as well as mouse TM4SF5 with a similar Kd value of ~2 nM (FIG. 3). These results show that the monoclonal antibody 2D4-18 of the present invention is useful for TM4SF5 protein detection.

Expression of TM4SF5 in Hepatocellular Carcinoma and Colon Cancer

It has been reported that TM4SF5 is expressed in colon carcinoma, pancreatic tumor, and HCC based on the mRNA expression determined by RT-PCR and Northern blotting. Here, we investigated the TM4SF5 expression in human HCC specimens by immunohistochemical staining with anti-TM4SF5 monoclonal antibody 2D4-18. As shown in FIG. 4 (B) and Table 1, all of the HCC tissues expressed TM4SF5 (staining in >11% of tumor cells). Analysis of 70 HCC specimens showed that 31% of HCC expressed TM4SF5 in >75% of tumor cells and 46% and 23% of HCC were positive for TM4SF5 expression in 74-50% and 49-11% of tumor cells, respectively (Table 1).

TABLE 1

| HCC tissue sections | | TM4SF5 positive | No. (%) cases staining TM4SF5 | | | |
|---|---|---|---|---|---|---|
| (AccuMax Array) | n | (%) | ≥75% | 74-50% | 49-11% | <10% |
| A204 | 35 | 100 | 10 (28) | 16 (46) | 9 (26) | 0 (0) |
| A204II | 35 | 100 | 12 (34) | 16 (46) | 7 (20) | 0 (0) |
| total | 70 | 100 | 22 (31) | 32 (46) | 16 (23) | 0 (0) |

In addition to HCC, expression of TM4SF5 was also detected in almost of the colon cancer tissues (98%, staining in >11% of tumor cells) as shown in FIG. 5 and Table 2. Analysis of 63 colon cancer specimens showed that 44% of colon cancer tissues expressed TM4SF5 in >75% of tumor cells and 37% and 17% of colon cancer tissues were positive for TM4SF5 expression in 74-50% and 49-11% of tumor cells, respectively. All the colon cancer patients with liver metastasis showed positive staining for TM4SF5 in colon cancer tissues as well as in liver cancer tissues (FIG. 5b).

TABLE 2

| Colon tissue sections | | TM4SF5 positive | No. (%) cases staining TM4SF5 | | | |
|---|---|---|---|---|---|---|
| (AccuMax Array) | n | (%) | ≥75% | 74-50% | 49-11% | <10% |
| A203III | 18 | 100 | 12 (67) | 5 (30) | 1 (0.5) | 0 (0) |
| A203VII | 45 | 100 | 16 (36) | 18 (40) | 10 (22) | 1 (2) |
| total | 63 | 100 | 28 (44) | 23 (37) | 11 (17) | 1 (2) |

Functional Effect of Anti-TM4SF5 Monoclonal Antibody 2D4-18 on Hepatocellular Carcinoma Cells and Colon Cancer Cells The expression of TM4SF5 was detected in HCC cells (Hep3B, Huh-7 and SNU-761) and colon cancer cells (HT-29, LoVo and CT-26) at the mRNA level as determined by RT-PCR (FIG. 6a). To investigate the effect of the anti-TM4SF5 monoclonal antibody 2D4-18 on cell growth, we performed MTT assay. The growth of Hep3B cells and Huh-7 cells expressing TM4SF5 was significantly delayed by antibody treatment (FIG. 6b).

In addition, we investigated the effect of the anti-TM4SF5 monoclonal antibody 2D4-18 on colon cancer cell growth. The growth of HT-29 cells, LoVo cells and CT-26 cells expressing TM4SF5 was delayed by antibody treatment (FIG. 6c).

These results clearly show that the monoclonal antibody of the present invention has anti-proliferative effect on cancer cells such as HCC cells and colon cancer cells.

Effect of Anti-TM4SF5 Monoclonal Antibody 2D4-18 on Migration of HCC Cells and Colon Cancer Cells The tetraspanin superfamily including TM4SF5 leads to integrin-mediated signaling pathways that are pivotal in cell migration/invasion and tumor cell motility. Therefore, we evaluated the influence of anti-TM4SF5 monoclonal antibody 2D4-18 on the cell migration and invasion. As shown in FIGS. 7 (A and B) and 8 (A and B), migration and invasion of TM4SF5-expressing cells was remarkably decreased by treatment of the cells with anti-TM4SF5 monoclonal antibody 2D4-18.

In addition, we performed wound healing assay. As shown in FIGS. 7 (c) and 8 (C), migration of Huh-7 cells and CT-26 cells to the wounded area was significantly reduced by treatment of the cells with anti-TM4SF5 monoclonal antibody 2D4-18.

These results confirm that anti-TM4SF5 monoclonal antibody (2D4-18)-mediated TM4SF5 targeting in cancer cells such as HCC cells and colon cancer cells can inhibit cell migration.

Targeting of Anti-TM4SF5 Monoclonal Antibody 2D4-18 on HCC Tumor

To evaluate targeting of anti-TM4SF5 monoclonal antibody 2D4-18 to HCC tumors in mice, anti-TM4SF5 monoclonal antibody 2D4-18 and normal mouse IgG was conjugated with DyLight 750-fluorescence and injected into the intraperitoneal cavity of tumor-developed BALB/c mice. After 72 hr, distribution of DyLight 750-labeled antibody was quantified by measuring the total photon flux (photons/s) of fluorescence. As shown in FIG. 9a, DyLight 750-labeled anti-TM4SF5 monoclonal antibody was localized in the tumors while DyLight 750-labeled normal IgG was not detected in the mice. When we took out the tumor mass and analyzed the microsection of the frozen tissues, we found that many of the tumor cells were stained with DyLight 750-labeled anti TM4SF5 antibody 2D4-18 (FIG. 9b). In contrast, we could not detect any labeling in the control section obtained from the mice injected with DyLight 750-labeled normal IgG.

These results show that anti-TM4SF5 monoclonal antibody 2D4-18 of the present invention can target tumor cells expressing TM4SF5 in vivo.

Anti-TM4SF5 Monoclonal Antibody 2D4-18 Inhibits HCC Tumor Growth in a Xenograft Mouse Model We observed the effect of TM4SF5-targeted monoclonal antibody on the growth of HCC cells in vivo using a xenograft mouse model. First, we injected nude mice subcutaneously in the dorsal right flank with Huh-7 cells and allowed the tumors to grow. When tumor size reached 5 mm in diameter, we dosed the animals twice a week in the intraperitoneal cavity with normal mouse IgG or anti TM4SF5 monoclonal antibody 2D4-18. Based on the tumor volume and weight, anti TM4SF5 antibody 2D4-18 attenuated the progression of HCC tumors compared with normal mouse IgG (A-C in FIG. 10). The antibody treatment did not affect the body weight during the experiment (D in FIG. 10). The expression of TM4SF5 in HCC tumor tissue was confirmed by immunostaining with anti-TM4SF5 monoclonal antibody 2D4-18 (E in FIG. 10).

Analysis of xenograft experiments revealed that anti TM4SF5 monoclonal antibody 2D4-18 targeting HCC tumor cells is sufficient to decrease tumor growth in vivo.

Anti-TM4SF5 Monoclonal Antibody 2D4-18 Inhibits HCC Tumor Growth in an Allograft Mouse Model To investigate the effect of anti-TM4SF5 monoclonal antibody 2D4-18 on HCC tumor development in an allograft mouse model, we used mouse BNL 1ME A.7R.1 HCC cell line (BNL-HCC cells) which was a chemically transformed mouse liver cell line derived from the normal BALB/c embryonic liver cell line, BNL CL2. As shown in FIG. 11 (A-C), anti-TM4SF5 monoclonal antibody 2D4-18 treatment significantly suppressed the progression of HCC tumors compared with the normal mouse IgG-treated control. The antibody treatment did not affect the body weight during the experiment (D in FIG. 11). The expression of TM4SF5 in HCC tumor tissue was also confirmed by immunostaining with anti-TM4SF5 monoclonal antibody 2D4-18 (E in FIG. 11).

Anti-TM4SF5 Monoclonal Antibody 2D4-18 Inhibits Colon Cancer Growth in a Xenograft Mouse Model We observed the effect of TM4SF5-targeted monoclonal antibody 2D4-18 on the growth of colon cancer cells in vivo using a xenograft mouse model. First, we injected nude mice subcutaneously in the dorsal right flank with HT-29 cells and allowed the tumors to grow. When tumor size reached 5 mm in diameter, we dosed the animals twice a week in the intraperitoneal cavity with normal mouse IgG or anti-TM4SF5 monoclonal antibody 2D4-18. Based on the tumor volume and weight, anti-TM4SF5 monoclonal antibody 2D4-18 attenuated the progression of colon tumors compared with normal mouse IgG (A-C in FIG. 12). The antibody treatment did not affect the body weight during the experiment (D in FIG. 12). The expression of TM4SF5 in colon tumor tissue was confirmed by immunostaining with anti-TM4SF5 monoclonal antibody 2D4-18 (E in FIG. 12).

Analysis of xenograft experiments revealed that anti-TM4SF5 monoclonal antibody 2D4-18 targeting colon tumor cells can decrease tumor growth in vivo.

Anti-TM4SF5 Monoclonal Antibody 2D4-18 Inhibits Colon Cancer Growth in an Allograft Mouse Model To investigate the effect of anti-TM4SF5 monoclonal antibody 2D4-18 on colon tumor development in an allograft mouse model, we used mouse CT-26 cells. As shown in FIG. 13 (A-C), treatment with anti-TM4SF5 monoclonal antibody 2D4-18 significantly suppressed the progression of colon tumors. The antibody treatment did not affect the body weight during the experiment (D in FIG. 13). The expression of TM4SF5 in colon tumor tissue was also confirmed by immunostaining with anti-TM4SF5 monoclonal antibody 2D4-18 (E in FIG. 13).

Anti-TM4SF5 Monoclonal Antibody 2D4-18 Inhibits Colon Cancer Metastasis in an Allograft Mouse Model For the metastatic cancer experiment, BALB/c mice were intravenously injected with mouse CT-26 colon cancer cells and then injected with PBS, IgG control, or anti-TM4SF5 monoclonal antibody 2D4-18. As shown in FIG. 14 (A-C), anti-TM4SF5 monoclonal antibody 2D4-18 inhibited development of lung cancer. Treatment with monoclonal antibody 2D4-18 suppressed loss of body weight induced by injection of CT-26 cells (D in FIG. 14).

Cloning of the Variable Domains of Anti-TM4SF5 Monoclonal Antibody 2D4-18

The cDNA sequences encoding the variable domains of heavy and light chains ($V_H$ and $V_L$) were cloned from hybridoma cells (2D4-18) producing anti-TM4SF5 monoclonal antibody 2D4-18. The sequences confirmed by DNA sequencing are shown in FIGS. 15 (2D4-18) and 16 (2D4-18(1)).

Expression of Recombinant Fab Derived from Anti-TM4SF5 Monoclonal Antibody 2D4-18

We used an expression vector pFabE for expression of recombinant Fab in *E. coli*. The pFabE includes the constant domain of κ light chain ($C_L$) and one constant domain of heavy chain ($C_{H1}$), and two cloning sites BstX I and Sfi I in which variable light domain ($V_L$) and heavy domain ($V_H$) can be inserted, respectively. We constructed a recombinant expression plasmids pFabE-2D4-18 and pFabE-2D4-18(1) by sequentially subcloning $V_L$ and $V_H$ sequences of 2D4-18 (A in FIG. 17). The recombinant plasmid directs bi-cistronic expression of $V_L$-$C_L$ fusion protein and $V_H$-$C_{H1}$ fusion protein under the control of LacZ promoter in *E. coli*. While $V_L$-$C_L$ fusion protein contains N-terminal OmpA tag and C-terminal Pre-S1 tag, $V_H$-$C_{H1}$ fusion protein includes N-terminal pelB tag and C-terminal His tag (B in FIG. 17). As both of $V_L$-$C_L$ fusion protein and $V_H$-$C_{H1}$ fusion protein have leader sequences for secretion, two proteins are secreted to the culture supernatant and self-assembled to generate a dimer protein, Fab (Jeon Y E, et al. *Mol Immunol* 44, 827-836(2007); Kwon Y S, et al. *Oncol Rep* 18, 513-517(2007)). We first performed 10 ml small scale culture and confirmed expression of recombinant $V_L$-$C_L$ fusion protein and $V_H$-$C_{H1}$ fusion protein using total cell lysates by western blotting analysis with anti-PreS1 antibody and anti-His antibody (FIG. 18). We also found 18° C. is better than 23° C. to control the expression of recombinant Fab using IPTG (FIG. 18). Then we performed large scale culture of *E. coli* and purified recombinant Fab-2D4-18 and Fab-2D4-18(1) of 2D4-18 from culture supernatant using Ni-NTA affinity column chromatography (FIGS. 19 and 20). As shown in FIG. 19 (A), SDS-PAGE in reducing condition and western blotting analysis revealed that a purified Fab-2D4-18 protein is composed of two polypeptides (recombinant heavy and light chains), and they are recognized by anti-His antibody and anti-Pre S1, respectively. In non-reducing condition, major protein band was found at the molecular weight of ~55 kDa, which is similar to the expected size of recombinant Fab (B in FIG. 19). As shown in FIG. 20 (A), SDS-PAGE in reducing and non-reducing condition revealed that a purified Fab-2D4-18(1) protein is composed of two polypeptides (recombinant heavy and light chains), and major protein band was found at the molecular weight of ~55 kDa. Western blotting analysis revealed that a purified Fab-2D4-18(1) protein is composed of two polypeptides (recombinant heavy and light chains), and each of them is recognized by anti-His antibody. In non-reducing condition, major protein band was found at the molecular weight of ~55 kDa, which is similar to the expected size of recombinant Fab (B in FIG. 20). To further confirm the functionality of the Fab, we quantitatively measured binding affinity of recombinant Fab-2D4-18 using Biacore. As a result, the Fab reacts with human TM4SF5 with a Kd value of ~0.15 μM (FIG. 21).

Functional Effect of Recombinant Fab of Anti-TM4SF5 Monoclonal Antibody 2D4-18 on Hepatocellular Carcinoma Cells To investigate the effect of recombinant Fab-2D4-18 and Fab-2D4-18(1) on cell growth, we performed MTT assay. While the growth of Hep3B cells and Huh-7 cells expressing TM4SF5 was significantly delayed by antibody treatment (FIGS. 22 and 23). These results indicate that recombinant Fab proteins of anti-TM4SF5 antibody 2D4-18 has antiproliferative effect.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. An antibody or antigen binding fragment thereof, that binds to TM4SF5 (transmembrane 4 superfamily member 5 protein), comprising:
   (a) a heavy chain variable domain comprising CDRH1 of SEQ ID NO:19, CDRH2 of SEQ ID NO:20, and CDRH3 of SEQ ID NO:21; and
   (b) a light chain variable domain comprising CDRL1 of SEQ ID NO:22, CDRL2 of SEQ ID NO:23, and CDRL3 of SEQ ID NO:24.

2. The antibody or antigen binding fragment thereof of claim 1, wherein the heavy chain variable domain comprises the amino acid sequence of SEQ ID NO:25 or SEQ ID NO:29.

3. The antibody or antigen binding fragment thereof of claim 1, wherein the light chain variable domain comprises the amino acid sequence of SEQ ID NO:26 or SEQ ID NO:30.

4. The antibody or antigen binding fragment thereof of claim 1, which comprises the following heavy and light chain variable domains:
   (i) a heavy chain variable domain of SEQ ID NO:25, and a light chain variable domain of SEQ ID NO:26; or
   (ii) a heavy chain variable domain of SEQ ID NO:29, and a light chain variable domain of SEQ ID NO:30.

5. The antibody or antigen binding fragment thereof of claim 1, which is produced from a hybridoma cell having an accession number KCLRF-BP-00291.

6. The antibody or antigen binding fragment thereof of claim 1, wherein the antigen binding fragment is Fab, F(ab'), F(ab')2 or Fv.

7. The antibody or antigen binding fragment thereof of claim 1, wherein the antibody is a monoclonal antibody, a polyclonal antibody, a chimeric antibody, a humanized antibody or a human antibody.

8. The antibody or antigen binding fragment thereof of claim 1, wherein the antibody is conjugated with a functional molecule.

9. The antibody or antigen binding fragment thereof of claim 8, wherein the functional molecule is a chemical substance, a radionuclide, a cytotoxin, a cytokine or a chemokine.

10. An antibody or antigen binding fragment thereof, that binds to TM4SF5 (transmembrane 4 superfamily member 5 protein), comprising CDRs of an antibody produced from a hybridoma cell having an accession number KCLRF-BP-00291.

11. A hybridoma cell line deposited under accession number KCLRF-BP-00291, producing an antibody that binds to TM4SF5 (transmembrane 4 superfamily member 5 protein).

12. A method for identifying the presence of TM4SF5 protein in a sample, using the antibody or antigen binding fragment thereof according to claim 1, wherein the method comprises the steps of contacting the antibody with the sample and detecting antibody bound to TM4SF5 protein in or from the sample.

13. The method of claim 12, wherein the sample is tissue, a cell, whole blood, serum, plasma, oral fluid, urine, lymph, or cerebrospinal fluid.

* * * * *

SEQUENCE LISTING

```
<160> NUMBER OF SEQ ID NOS: 32

<210> SEQ ID NO 1
<211> LENGTH: 22
<212> TYPE: DNA
<213> ORGANISM: Artificial Sequence
<220> FEATURE:
<223> OTHER INFORMATION: forward primer for mouse GAPDH

<400> SEQUENCE: 1
atggtgaagg tcggtgtgaa cg                                              22

<210> SEQ ID NO 2
<211> LENGTH: 22
<212> TYPE: DNA
<213> ORGANISM: Artificial Sequence
<220> FEATURE:
<223> OTHER INFORMATION: reverse primer for mouse GAPDH

<400> SEQUENCE: 2
gttgtcatgg atgatcttgg cc                                              22

<210> SEQ ID NO 3
<211> LENGTH: 20
<212> TYPE: DNA
<213> ORGANISM: Artificial Sequence
<220> FEATURE:
```

```
<223> OTHER INFORMATION: forward primer for mouse TM4SF5

<400> SEQUENCE: 3
cgcttacttg cgaaatgaca                                              20

<210> SEQ ID NO 4
<211> LENGTH: 20
<212> TYPE: DNA
<213> ORGANISM: Artificial Sequence
<220> FEATURE:
<223> OTHER INFORMATION: reverse primer for mouse TM4SF5

<400> SEQUENCE: 4
tttcctgcaa tcgccacaca                                              20

<210> SEQ ID NO 5
<211> LENGTH: 20
<212> TYPE: DNA
<213> ORGANISM: Artificial Sequence
<220> FEATURE:
<223> OTHER INFORMATION: forward primer for human beta-actin

<400> SEQUENCE: 5
gggtcagaag gattcctatg                                              20

<210> SEQ ID NO 6
<211> LENGTH: 21
<212> TYPE: DNA
<213> ORGANISM: Artificial Sequence
<220> FEATURE:
<223> OTHER INFORMATION: reverse primer for human beta-actin

<400> SEQUENCE: 6
ccttaatgtc acgcacgatt t                                            21

<210> SEQ ID NO 7
<211> LENGTH: 20
<212> TYPE: DNA
<213> ORGANISM: Artificial Sequence
<220> FEATURE:
<223> OTHER INFORMATION: forward primer for human TM4SF5

<400> SEQUENCE: 7
agcttgcaag tctggctcat                                              20

<210> SEQ ID NO 8
<211> LENGTH: 20
<212> TYPE: DNA
<213> ORGANISM: Artificial Sequence
<220> FEATURE:
<223> OTHER INFORMATION: reverse primer for human TM4SF5

<400> SEQUENCE: 8
gctggatccc acacagtact                                              20

<210> SEQ ID NO 9
<211> LENGTH: 32
<212> TYPE: DNA
<213> ORGANISM: Artificial Sequence
<220> FEATURE:
<223> OTHER INFORMATION: IGG2A primer

<400> SEQUENCE: 9
ggaagatctc ttgaccaggc atcctagagt ca                                32
```

-continued

```
<210> SEQ ID NO 10
<211> LENGTH: 35
<212> TYPE: DNA
<213> ORGANISM: Artificial Sequence
<220> FEATURE:
<223> OTHER INFORMATION: 5'MH2 primer
<220> FEATURE:
<221> NAME/KEY: misc_feature
<222> LOCATION: (18)..(18)
<223> OTHER INFORMATION: n is a, c, g, or t

<400> SEQUENCE: 10
cttccggaat tcsargtnma gctgsagsag tcwgg                                35

<210> SEQ ID NO 11
<211> LENGTH: 30
<212> TYPE: DNA
<213> ORGANISM: Artificial Sequence
<220> FEATURE:
<223> OTHER INFORMATION: 3'Kc primer

<400> SEQUENCE: 11
ggtgcatgcg gatacagttg gtgcagcatc                                      30

<210> SEQ ID NO 12
<211> LENGTH: 32
<212> TYPE: DNA
<213> ORGANISM: Artificial Sequence
<220> FEATURE:
<223> OTHER INFORMATION: 5'Mk primer

<400> SEQUENCE: 12
gggagctcga yattgtgmts acmcarwctm ca                                   32

<210> SEQ ID NO 13
<211> LENGTH: 37
<212> TYPE: DNA
<213> ORGANISM: Artificial Sequence
<220> FEATURE:
<223> OTHER INFORMATION: forward primer for VH

<400> SEQUENCE: 13
ggcccagccg gccatggccc aggtccagct ggagcag                              37

<210> SEQ ID NO 14
<211> LENGTH: 30
<212> TYPE: DNA
<213> ORGANISM: Artificial Sequence
<220> FEATURE:
<223> OTHER INFORMATION: reverse primer for VH

<400> SEQUENCE: 14
ggccgtgctg gccgaggaga ctgtgagagt                                      30

<210> SEQ ID NO 15
<211> LENGTH: 37
<212> TYPE: DNA
<213> ORGANISM: Artificial Sequence
<220> FEATURE:
<223> OTHER INFORMATION: forward primer for VH(1)

<400> SEQUENCE: 15
ggcccagccg gccatggccg ggagacttag tgaagcc                              37

<210> SEQ ID NO 16
<211> LENGTH: 65
<212> TYPE: DNA
```

<210> SEQ ID NO 16
<211> LENGTH: 65
<212> TYPE: DNA
<213> ORGANISM: Artificial Sequence
<220> FEATURE:
<223> OTHER INFORMATION: forward primer for VL

<400> SEQUENCE: 16
ccattgcagt ggcactggct ggtttcgcta ccgtagcaca ggcagccgat attgtgatga   60
cccag                                                              65

<210> SEQ ID NO 17
<211> LENGTH: 28
<212> TYPE: DNA
<213> ORGANISM: Artificial Sequence
<220> FEATURE:
<223> OTHER INFORMATION: reverse primer for VL

<400> SEQUENCE: 17
ccaccgtact ggcccgtttt atttccaa                                     28

<210> SEQ ID NO 18
<211> LENGTH: 60
<212> TYPE: DNA
<213> ORGANISM: Artificial Sequence
<220> FEATURE:
<223> OTHER INFORMATION: forward primer for VL(1)

<400> SEQUENCE: 18
ccattgcagt ggcactggct ggtttcgcta ccgtagcaca ggcagccctc tccctgcctg   60

<210> SEQ ID NO 19
<211> LENGTH: 10
<212> TYPE: PRT
<213> ORGANISM: Artificial Sequence
<220> FEATURE:
<223> OTHER INFORMATION: CDRH1

<400> SEQUENCE: 19

Gly Phe Thr Phe Ser Ser Tyr Gly Met Ser
1               5                   10

<210> SEQ ID NO 20
<211> LENGTH: 8
<212> TYPE: PRT
<213> ORGANISM: Artificial Sequence
<220> FEATURE:
<223> OTHER INFORMATION: CDRH2

<400> SEQUENCE: 20

Ile Ser Ser Gly Gly Gly Tyr Thr
1               5

<210> SEQ ID NO 21
<211> LENGTH: 13
<212> TYPE: PRT
<213> ORGANISM: Artificial Sequence
<220> FEATURE:
<223> OTHER INFORMATION: CDRH3

<400> SEQUENCE: 21

Ala Arg His Glu Gly Phe Thr Thr Tyr Tyr Phe Asp Tyr
1               5                   10

<210> SEQ ID NO 22
<211> LENGTH: 16
<212> TYPE: PRT
<213> ORGANISM: Artificial Sequence
<220> FEATURE:

<223> OTHER INFORMATION: CDRL1

<400> SEQUENCE: 22

Arg Ser Ser Gln Ser Ile Leu His Ser Ser Gly Asn Thr Tyr Leu Glu
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: CDRL2

<400> SEQUENCE: 23

Lys Val Ser Asn Arg Phe Ser
1               5

<210> SEQ ID NO 24
<211> LENGTH: 9
<212> TYPE: PRT
<213> ORGANISM: Artificial Sequence
<220> FEATURE:
<223> OTHER INFORMATION: CDRL3

<400> SEQUENCE: 24

Phe Gln Gly Ser His Val Pro Phe Thr
1               5

<210> SEQ ID NO 25
<211> LENGTH: 112
<212> TYPE: PRT
<213> ORGANISM: Artificial Sequence
<220> FEATURE:
<223> OTHER INFORMATION: variable domain of heavy chain

<400> SEQUENCE: 25

Gly Asp Leu Val Lys Pro Gly Gly Ser Leu Lys Leu Ser Cys Ala Ala
1               5                   10                  15

Ser Gly Phe Thr Phe Ser Ser Tyr Gly Met Ser Trp Val Arg Gln Thr
            20                  25                  30

Pro Asp Lys Arg Leu Glu Trp Val Ala Thr Ile Ser Ser Gly Gly Gly
        35                  40                  45

Tyr Thr Tyr Tyr Pro Asp Ser Val Lys Gly Arg Phe Thr Ile Ser Arg
    50                  55                  60

Asp Asn Ala Lys Asn Thr Leu Tyr Leu Gln Met Arg Ser Leu Lys Ser
65                  70                  75                  80

Glu Asp Thr Ala Met Tyr Tyr Cys Ala Arg His Glu Gly Phe Thr Thr
                85                  90                  95

Tyr Tyr Phe Asp Tyr Trp Gly Gln Gly Thr Thr Leu Thr Val Ser Ser
            100                 105                 110

<210> SEQ ID NO 26
<211> LENGTH: 105
<212> TYPE: PRT
<213> ORGANISM: Artificial Sequence
<220> FEATURE:
<223> OTHER INFORMATION: variable domain of light chain

<400> SEQUENCE: 26

Leu Ser Leu Pro Val Ser Leu Gly Asp Gln Ala Ser Ile Ser Cys Arg
1               5                   10                  15

Ser Ser Gln Ser Ile Leu His Ser Ser Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
 50                  55                  60

Gly Thr Asp Phe Thr Leu Lys Ile Ser Arg Val Glu Ala Glu Asp Leu
 65                  70                  75                  80

Gly Val Tyr Tyr Cys Phe Gln Gly Ser His Val Pro Phe Thr Phe Gly
                 85                  90                  95

Ser Gly Thr Lys Leu Glu Ile Lys Arg
            100                 105

<210> SEQ ID NO 27
<211> LENGTH: 338
<212> TYPE: DNA
<213> ORGANISM: Artificial Sequence
<220> FEATURE:
<223> OTHER INFORMATION: variable domain of heavy chain

<400> SEQUENCE: 27
gggagactta gtgaagcctg gagggtccct gaaactctcc tgtgcagcct ctggattcac      60
tttcagtagc tatggcatgt cttgggttcg ccagactcca gacaagaggc tggagtgggt     120
cgcaaccatt agtagtggtg gtggttacac ctactatcca gacagtgtga aggggcgatt     180
caccatctcc agagacaatg ccaagaacac cctgtacctg caaatgcgca gtctgaagtc     240
tgaggacaca gccatgtatt actgtgcaag acatgagggc tttacgacgt actactttga     300
ctactggggc caaggcacca ctctcacagt ctcctcag                             338

<210> SEQ ID NO 28
<211> LENGTH: 316
<212> TYPE: DNA
<213> ORGANISM: Artificial Sequence
<220> FEATURE:
<223> OTHER INFORMATION: variable domain of light chain

<400> SEQUENCE: 28 ctctcccctgc ctgtcagtct tggagatcaa gcctccatct cttgcagatc tagtcagagc     60
attttacata gttctggaaa cacctattta aatggtacc tgcagaaacc aggccagtct      120
ccaaagctcc tgatctacaa agtttccaac cgatttttctg gggtcccaga caggttcagt    180
ggcagtggat cagggacaga tttcacactc aagatcagca gagtggaggc tgaggatctg    240
ggagtttatt actgctttca aggttcacat gttccattca cgttcggctc ggggacaaag    300
ttggaaataa aacggg                                                     316

<210> SEQ ID NO 29
<211> LENGTH: 120
<212> TYPE: PRT
<213> ORGANISM: Artificial Sequence
<220> FEATURE:
<223> OTHER INFORMATION: variable domain of heavy chain (1)

<400> SEQUENCE: 29

Gln Val Gln Leu Glu Gln Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Gly Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Arg Ser Leu Lys Ser Glu Asp Thr Ala Met Tyr Tyr Cys
                 85                  90                  95

Ala Arg His Glu Gly Phe Thr Thr Tyr Tyr Phe Asp Tyr Trp Gly Gln
             100                 105                 110

Gly Thr Thr Leu Thr Val Ser Ser
            115                 120

<210> SEQ ID NO 30
<211> LENGTH: 113
<212> TYPE: PRT
<213> ORGANISM: Artificial Sequence
<220> FEATURE:
<223> OTHER INFORMATION: variable domain of light chain (1)

<400> SEQUENCE: 30

Asp Ile Val Met Thr Gln Ser Pro Leu Ser Leu Pro Val Ser Leu Gly
 1               5                  10                  15

Asp Gln Ala Ser Ile Ser Cys Arg Ser Ser Gln Ser Ile Leu His Ser
             20                  25                  30

Ser Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
             100                 105                 110

Arg

<210> SEQ ID NO 31
<211> LENGTH: 361
<212> TYPE: DNA
<213> ORGANISM: Artificial Sequence
<220> FEATURE:
<223> OTHER INFORMATION: variable domain of heavy chain (1)

<400> SEQUENCE: 31
caggtccagc tggagcagtc tgggggagac ttagtgaagc ctggagggtc cctgaaactc    60
tcctgtgcag cctctggatt cactttcagt agctatggca tgtcttgggt tcgccagact   120
ccagacaaga ggctggagtg ggtcgcaacc attagtagtg gtggtggtta cacctactat   180
ccagacagtg tgaaggggcg attcaccatc tccagagaca tgccaagaa caccctgtac   240 ctgcaaatgc gcagtctgaa gtctgaggac acagccatgt attactgtgc aagacatgag   300
ggctttacga cgtactactt tgactactgg ggccaaggca ccactctcac agtctcctca   360
g                                                                  361

<210> SEQ ID NO 32
<211> LENGTH: 340
<212> TYPE: DNA
<213> ORGANISM: Artificial Sequence
<220> FEATURE:
<223> OTHER INFORMATION: variable domain of light chain (1)

```
<400> SEQUENCE: 32
gatattgtga tgacccagtc tccactctcc ctgcctgtca gtcttggaga tcaagcctcc        60
atctcttgca gatctagtca gagcatttta catagttctg gaaacaccta tttagaatgg       120
tacctgcaga aaccaggcca gtctccaaag ctcctgatct acaaagtttc caaccgattt       180
tctggggtcc cagacaggtt cagtggcagt ggatcaggga cagatttcac actcaagatc       240
agcagagtgg aggctgagga tctgggagtt tattactgct ttcaaggttc acatgttcca       300
ttcacgttcg gctcggggac aaagttggaa ataaaacggg                             340
```